US008119653B2

(12) United States Patent
Romo et al.

(10) Patent No.: US 8,119,653 B2
(45) Date of Patent: Feb. 21, 2012

(54) BELACTOSIN DERIVATIVES AS THERAPEUTIC AGENTS/BIOLOGICAL PROBES AND THEIR SYNTHESIS

(75) Inventors: Daniel Romo, College Station, TX (US); Sung Wook Cho, College Station, TX (US); Jeffrey W. Smith, San Diego, CA (US); Robyn D. Richardson, San Diego, CA (US)

(73) Assignee: The Texas A&M University System, College Station, TX (US)

( * ) Notice: Subject to any disclaimer, the term of this patent is extended or adjusted under 35 U.S.C. 154(b) by 838 days.

(21) Appl. No.: 11/775,154

(22) Filed: Jul. 9, 2007

(65) Prior Publication Data

US 2009/0042922 A1 Feb. 12, 2009

Related U.S. Application Data

(60) Provisional application No. 60/819,213, filed on Jul. 7, 2006.

(51) Int. Cl.
*A61K 31/436* (2006.01)
*C07D 221/18* (2006.01)

(52) U.S. Cl. .................................... 514/279; 546/37
(58) Field of Classification Search .................. 514/449, 514/279; 549/263; 546/37
See application file for complete search history.

(56) References Cited

U.S. PATENT DOCUMENTS

| | | | | |
|---|---|---|---|---|
| 5,663,298 | A | 9/1997 | Mizukami et al. | ............. 530/332 |
| 7,223,745 | B2 | 5/2007 | Chatterjee et al. | .............. 514/64 |

FOREIGN PATENT DOCUMENTS

| | | |
|---|---|---|
| EP | 768317 * | 4/1997 |
| EP | 1 166 781 | 2/2002 |
| WO | WO 00/43000 | 7/2000 |
| WO | WO 2004/007506 | 1/2004 |

OTHER PUBLICATIONS

Caller et al., "Formation of disubstituted beta-lactones using bifunctional catalysis," *Org. Lett.*, 7:1809-1812, 2005.
Cortez et al., "Intramolecular, nucleophile-catalyzed aldol-lactonization (NCAL) reactions: catalytic, asymmetric synthesis of bicyclic beta-lactones," *J. Am. Chem. Soc.*, 123:7945-7946, 2001.
Enders and Kallfass, "An efficient nucleophilic carbene catalyst for the asymmetric benzoin condensation," *ACIE*, 41:1743-1745, 2002.
France, S. et al., "Nucleophilic Chiral Amines as Catalysts in Asymmetric Synthesis," *Chem. Rev.*, 103:2985-3012, 2003.
Getzler et al., "Synthesis of beta-lactones: a highly active and selective catalyst for epoxide carbonylation," *J. Am. Chem. Soc.*, 124:1174-1175, 2002.
Kerr and Rovis, "Effect of the michael acceptor in the asymmetric intramolecular stetter reaction," *Synlett.*, 12:1934-1936, 2003.
Kerr et al., "A highly enantioselective catalytic intramolecular Stetter reaction," *J. Am. Chem. Soc.*, 124:10298-10299, 2002.
Lall et al., "Serine and threonine beta-lactones: a new class of hepatitis A virus 3C cysteine proteinase inhibitors," *J. Org. Chem.*, 67:1536-1547, 2002.
Lowe and Vederas, "Naturally ocurring β-lactones: occurrence, syntheses and properties. A review," *Org. Prep. Proceed. Int.*, 27:305-346, 1995.
Oh et al., "Asymmetric synthesis of bicyclic β-lactones via the intramolecular, nucleophile-catalyzed aldol lactonization: improved efficiency and expanded scope," *J. Org. Chem.* 70:2835-2838, 2005.
Pommier and Pons, "Recent advances in ⊖-lactone chemistry," *Synthesis*, pp. 441-459, 1993.
Ramiandrasoa et al., "Poly(β-malic acid alkyl esters) derived from 4-alkyloxycarbonyl-2-oxetanones obtained via the ketene route," *Vert, M. Polym. Bull.*, 30:501-508, 1993.
Rieth et al., "Single-site beta-diiminate zinc catalysts for the ring-opening polymerization of beta-butyrolactone and beta-valerolactone to poly(3-hydroxyalkanoates)," *J. Am. Chem. Soc.*, 124:15239-15248, 2002.
Romo et al., U.S. Appl. No. 11/775,216, "Cyclic-fused beta-lactones and their synthesis," filed Jul. 9, 2007.
Seitzberg et al., "Design and synthesis of a new type of ferrocene-based planar chiral DMAP analogues. A new catalyst system for asymmetric nucleophilic catalysis," *J. Org. Chem.*, 70:8332-8337, 2005.
Wang et al., "β-Lactones as Intermediates for Natural Product Total Synthesis and New Transformations," *Heterocycles*, 64:605-658, 2004.
Wilson and Fu, "Asymmetric Synthesis of Highly Substituted-Lactones by Nucleophile-Catalyzed [2+2] Cycloadditions of Disubstituted Ketenes with Aldehydes," *Angew. Chem. Int.* 116:6518-6520, 2004.
Wynberg and Staring, "Asymmetric synthesis of (S)- and (R)-malic acid from ketene and chloral," *J. Am. Chem. Soc.*, 104:166-168, 1982.
Wynberg and Staring, "Catalytic asymmetric synthesis of chiral 4-substituted 2-oxetanones," *J. Org. Chem.*, 50:1977-1979, 1985.
Wynberg, "Asymmetric Catalysis by Alkaloids," *Stereochem.*, 16:87-130, 1986.
Yang and Romo, "Methods for the Synthesis of Optically Active b-Lactones (2-Oxetanones)," *Tetrahedron*, 55:6403-6434, 1999.
Zhu et al., "Cinchona alkaloid-lewis acid catalyst systems for enantioselective ketene-aldehyde cycloadditions," *J. Am. Chem. Soc.*, 126:5352-5353, 2004.
International Preliminary Report on Patentability issued Jan. 13, 2009, (Published Jan. 13, 2009) during the prosecution of Intl. Appl. No. PCT/US2007/073077.
International Search Report issued Dec. 17, 2007, (Published Feb. 28, 2008) during the prosecution of International Appl. No. PCT/US2007/073077.
Written Opinion issued Dec. 17, 2007, (Published Jan. 7, 2009) during the prosecution of International Appl.No. PCT/US2007/073077.

(Continued)

*Primary Examiner* — Taofiq A Solola
(74) *Attorney, Agent, or Firm* — Christensen O'Connor Johnson Kindness PLLC

(57) ABSTRACT

Derivatives of belactosin and their synthesis are disclosed. In certain embodiments, compounds of the present invention exhibit anti-cancer, antiviral, antibiotic, and/or auto-immune therapeutic abilities. In general, methods of synthesis disclosed herein allow for introduction of a variety of substituents at numerous positions as well as the facile introduction of a beta-lactone ring moiety. The synthetic steps comprise, in preferred embodiments, a tandem Mukaiyama aldol lactonization reaction. Data demonstrating the utility of some of the derivatives as proteasome inhibitors is also disclosed.

32 Claims, 3 Drawing Sheets

OTHER PUBLICATIONS

Adams et al., "Proteasome inhibition: a new strategy in cancer treatment," *Invest. New Drugs*, 18:109-121, 2000.
Adams et al., "Proteasome inhibitors: a novel class of potent and effective antitumor agents," *Cancer Res.*, 59:2615-2622, 1999.
Adams, "Preclinical and clinical evaluation of proteasome inhibitor PS-341 for the treatment of cancer," *Curr.Opin. Chem. Biol.*, 6:493-500, 2002a.
Adams, "Proteasome inhibition: a novel approach to cancer therapy," *Trends Mol. Med.*, 8:S49-54, 2002b.
Akaishi et al., "Purification and properties of the 26S proteasome from the rat brain: evidence for its degradation of myelin basic protein in a ubiquitin-dependent manner," *Brain Res.*, 722:139-144, 1996.
Asai et al., "A new structural class of proteasome inhibitors identified by microbial screening using yeast-based assay," *Biochem. Pharm.*, 67:227-234, 2004.
Asai et al., "Belactosin A, a novel antitumor antibiotic acting on cyclin/CDK mediated cell cycle regulation, produced by *Streptomyces* sp," J. Antibiot., 53:81-83, 2000.
Browne et al., "Inhibition of endothelial cell proliferation and angiogenesis by orlistat, a fatty acid synthase inhibitor," *FASEB J.*, 20:2027-2035, 2006.
Cho and Romo, "Total synthesis of (−)-belactosin C and derivatives via double diastereoselective tandem mukaiyama aldol lactonizations," *Org. Lett.*, 9:1537-1540, 2007.
Garcia-Echeverria, "Peptide and peptide-like modulators of 20S proteasome enzymatic activity in cancer cell," *Int. J. Pep. Res. Therap.*, 12:49-64, 2006.
Garcia-Echeverria, "Recent advances in the identification and development of 20S proteasome inhibitors," *Mini Reviews in Medicinal Chemistry*, 2:247-259, 2002.
Groll et al., "Inhibitor-binding mode of homobelactosin C to proteasomes: new insights into classI MHC ligand generation," *PNAS*, 103:4576-4679, 2006.
Hirano et al., "Large- and small-scale purification of mammalian 26S proteasomes," *Methods Enzymol.*, 399:227-240, 2005.
Jenni et al., "Architecture of a fungal fatty acid synthase at 5 A Resolution," *Science*, 311:1263, 2006.
Knowles et al., "A fatty acid synthase blockade induces tumor cell-cycle arrest by down-regulating Skp2," *J. Biol. Chem.*, 279:30540, 2004.
Kridel et al., "Orlistat is a novel inhibitor of fatty acid synthase with antitumor activity," *Cancer*, 64:2070-2075, 2004.
Kumaraswamy and Markondaiah, "Stereoselective synthesis of belactosin C and its derivatives using a catalytic proline catalyzed crossed-aldol reaction," *Tet. Lett.*, 48:1707-1709, 2007.
Kumaraswamy et al., Oppolzer sultam directed aldol as a key step for the stereoselective syntheses of antitumor antibiotic belactosin C and its synthetic congeners, *J. Org. Chem.*, 71:337-340, 2006.
Larionov and de Meijere, "Enantioselective total synthesis of Belactosin A, Belactosin C, and its homoanalogue," *Org. Lett.*, 6:2153-2156, 2004.
Ma et al., "Concise total synthesis of (±)-salinosporamide A, (±)-cinnabaramide A, and derivatives via a bis-cyclization process: implications for a biosynthetic pathway?," *Organic Letters*, 9:2143-2146, 2007.
Maier et al., "Architecture of mammalian fatty acid synthase at 4.5 A resolution," *Science*, 311:1258, 2006.
Mellgren, "Specificities of cell permeant peptidyl inhibitors for the proteinase activities of mu-calpain and the 20 S proteasome," *J. Biol. Chem.*, 272:29899-29903, 1997.
Murray et al., "Proteasome inhibitors as anti-cancer agents," *Anti-cancer Drugs*, 11:407-417, 2000.
Pizer et al., "Fatty acid synthase (FAS): a target for cytotoxic antimetabolites in HL60 promyelocytic leukemia cells," *Cancer Res.*, 56:745-751, 1996.
Prasad and Chandrakumar, "Asymmetric synthesis of α-methoxyarylacetic acid derivatives," *Tetrahedron: Asymmetry*, 16:1897-1900, 2005.
Purohit et al., "Practical, catalytic, asymmetric synthesis of beta-lactones via a sequential ketene dimerization/hydrogenation process: inhibitors of the thioesterase domain of fatty acid synthase," *J. Org. Chem.*, 71:4549-4958, 2006.
Riyad et al., "Bicyclic- and tricyclic-β-lactones via organonucleophile-promoted bis-cyclizations of keto acids: enantioselective synthesis of (+)-dihydroplakevulin," *Organic Letters*, 8:4363-4366, 2006.
Scutt, "EMD273316 & EMD95833, type 4 phosphodiesterase inhibitors, stimulate fibroblastic-colony formation by bone marrow cells via direct inhibition of PDE4 and the induction of endogenous prostaglandin synthesis," *BMC Pharmacol.*, 4:10, 2004.
Ugai et al., "Purification and characterization of the 26S proteasome complex catalyzing ATP-dependent breakdown of ubiquitin-ligated proteins from rat liver," *J. Biochem. (Tokyo)*, 113:754-768, 1993.
Yang and Romo, "Practical, one-step synthesis of optically active β-lactones via the tandem mukaiyama aldol-lactonization (TMAL) reaction," *J. Org. Chem.*, 63:1344-1347, 1998.
Yang et al., "Studies of the tandem mukaiyma aldol-lactonization (TMAL) reaction: a concise and highly diastereoselective route to β-lactones applied to the total synthesis of the potent pancreatice lipase inhibitor, (−)-panclicin-D," *Tetrahedron*, 53:16471-16488, 1997.

* cited by examiner

Synthesis of Dipeptide

Synthesis of β-lactone

Coupling of β-lactone and dipeptide

BELACTOSIN DERIVATIVES AS THERAPEUTIC AGENTS/BIOLOGICAL PROBES AND THEIR SYNTHESIS

This application claims the benefit of U.S. Provisional Application No. 60/819,213 filed Jul. 7, 2006, the contents of which are incorporated herein in their entirety.

This invention was made with government support under CHE-0416260 awarded by the National Science Foundation (NSF). The government has certain rights in the invention.

BACKGROUND OF THE INVENTION

A. Field of the Invention

The present invention relates generally to derivatives of belactosin and their synthesis. Certain belactosin derivatives of the present invention are inhibitors of both fatty acid synthase and the proteasome. As such, these derivatives, in certain embodiments, are candidates as anticancer and/or autoimmune therapeutics, antivirals, or antibiotics. The synthesis of these compounds generally comprises a concise, single step formation of a common beta-lactone (2-oxetanone) moiety.

B. Background of the Invention

Belactosin and its derivatives have recently garnered interest in the scientific community due to their potential anticancer activities. Initial studies of the belactosins revealed that these molecules could represent good lead compounds for cancer treatment by regulating the ubiquitin-proteasome pathways. Mizukami et al., 1997; Asai et al., 2004. The ubiquitin-proteasome pathway generates peptide products with a narrow length distribution centered around 8-12 mers, a size suitable for binding to MHC class 1 molecules. Groll et al., 2005; Michalek et al., 1993. This process allows $CD8^+$ T lymphocytes to identify and eliminate cells that are synthesizing abnormal or "foreign" proteins, as may arise through mutations or infection by viruses. Cresswell et al., 1999. The 20S proteasome is the central component of this degradation system. Kumaraswamy et al., 2006. Certain belactosins have been shown to exhibit behavior similar to that of lactacystin, an inhibitor of the 20S proteasome. Kumaraswamy et al., 2006. Proteasome inhibitors represent a novel anticancer therapy. Adams et al., 2000; Murray et al., 2000; Adams et al., 1999; Adams et al., 2002a; Adams et al., 2002b. It has been shown that belactosins A and C arrest cell-cycle progression at the G2/M phase. Asai et al., 2000. Belactosin and its derivatives feature a beta-lactone ring, and this moiety is pivotal for bioactivity. Kumaraswamy et al., 2006. Thus, synthetic derivatives of belactosin featuring this moiety are potential therapeutic targets of the proteasome.

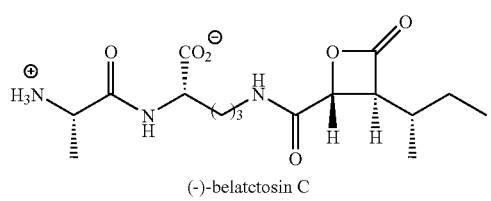

(-)-belatctosin C

Orlistat, a drug approved for treating obesity, also features such a beta-lactone ring moiety. Purohit et al., 2006; Kridel et al., 2004; Knowles et al., 2004. This drug has recently been shown to be a potent inhibitor of human fatty acid synthase (FAS); further, this natural product derivative is cytotoxic and cytostatic to tumor cells in vitro and can inhibit tumor growth in vivo. Kridel et al., 2004; Knowles et al., 2004. FAS is responsible for the cellular synthesis of palmitate and is attracting great interest as a drug target in oncology because it is up-regulated in most solid tumors, including those of the breast, prostate and ovary. Purohit et al., 2006; Alo et al., 1996; Swinnen et al., 2002; Rossi et al., 2003; Pizer et al., 1996a; Pizer et al., 1996b; Pizer et al., 2000; Pizer et al., 2001; Gansler et al., 1997. Furthermore, a number of studies show that a pharmacologic blockade of FAS can be cytostatic and cytotoxic to tumor cells. Kuhajda et al., 2000; Kuhajda et al., 1994; Pizer et al., 1998; Funabashi et al. 1989; Pizer et al., 2000. However, orlistat has poor solubility and poor bioavailability, so there is a need to develop new beta-lactones that overcome these problems and that can be deployed as potential antitumor drugs. In addition, simplified derivatives that are readily prepared would also ultimately be attractive from the standpoint of process development.

Previous syntheses of belactosin and derivatives have relied on multi-step syntheses of the beta-lactone moiety involving, for example, aldol chemistry followed by a subsequent lactonization step. In addition, syntheses to date have focused on synthesis of appropriate beta-lactones followed by coupling to a dipeptide. To date, there have been three known reports of syntheses of belactosin and derivatives. Armstrong and Scutt, 2004; Larionov and de Meijere, 2004; Kumaraswamy et al., 2006. Improved methods of preparing belactosin and derivatives are needed, such as methods involving fewer synthetic steps.

SUMMARY OF THE INVENTION

The present invention overcomes deficiencies in the art by providing novel derivatives of belactosin comprising a beta-lactone ring structure. A particularly attractive feature of certain compounds of the present invention is their ability, in certain embodiments, to act as inhibitors of the proteasome and/or FAS. This inhibitory activity significantly increases the therapeutic potential of these compounds. For example, certain compounds of the present invention are low nanomolar inhibitors of the 20S proteasome. As such, these compounds could be used in treatments for cancer as well as malaria, tuberculosis and other indications. Indeed, any protein that recognizes the beta-lactone moiety as a substrate may recognize a compound as described herein.

Further, the present invention contemplates, in certain embodiments, a concise synthesis of these compounds that allows access to a variety of beta-lactones in a diastereoselective manner, often in fewer steps than disclosed in previous methodologies. In preferred embodiments, the synthetic steps comprise a tandem Mukaiyama aldol lactonization (TMAL) reaction. Other compounds comprising a beta-lactone moiety besides belactosins include the vegetal poison anisatin and the antibiotic 1233A (Kumaraswamy and Markondaiah, 2007): such compounds may also be accessed via methods of the present invention.

Accordingly, compounds of the present invention are generally drawn to compounds of formula (X):

wherein $X_0$ is a chiral auxiliary, such as

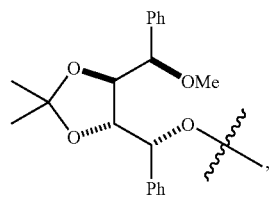

or $X_0$ is a compound of formula (I):

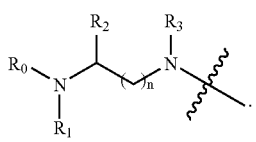

(I)

Within formula (X), $R_0$ may be selected from a group consisting of H, alkyl, an amine protecting group and

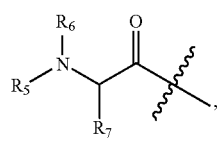

wherein $R_5$ and $R_6$ may each independently be selected from the group consisting of H, alkyl, aryl, an amine protecting group and

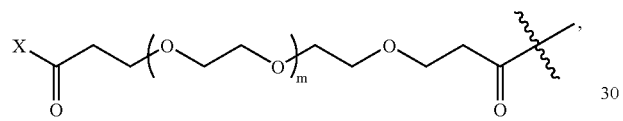

wherein m may range in length from 1-5, depending on the desired length of this flexible linker, and X may comprise a fluorophore. Other linkers or spacers known to those of skill in the art may also be employed. Linkers or spacers typically are of low reactivity and are internally flexible moieties that allow one moiety to be joined with another at a desired distance. Fluorophores and methods of incorporation into various compounds are well known to those of skill in the art. See, e.g., FluoProbes® BioDirectory of Fluorescence; Molecular Probes, The Handbook—A Guide to Fluorescent Probes and Labeling Technologies, 10$^{th}$ Ed. (2005), both of which are herein incorporated by reference in their entirety. Compounds of the present invention comprising a fluorophore may be useful as tools (e.g., biological probes) for studying proteins, in vivo or in vitro, such as FAS, the proteasome, and various enzymes and other proteins that recognize beta-lactone rings of the present invention. In preferred embodiments, the fluorophore may be selected from the group consisting of:

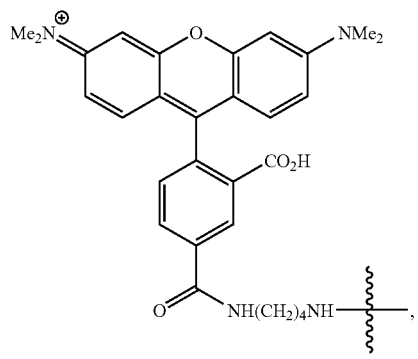

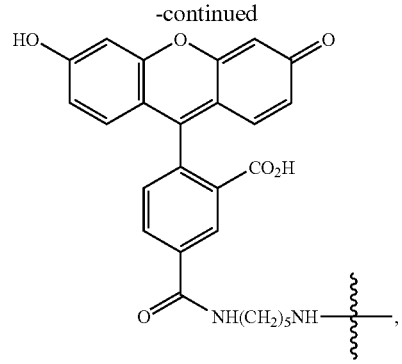

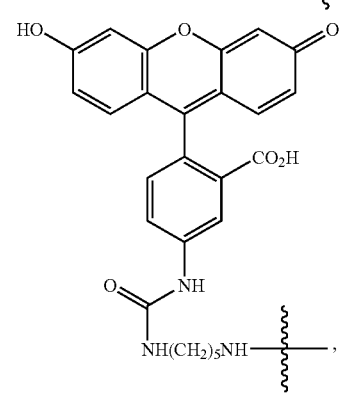

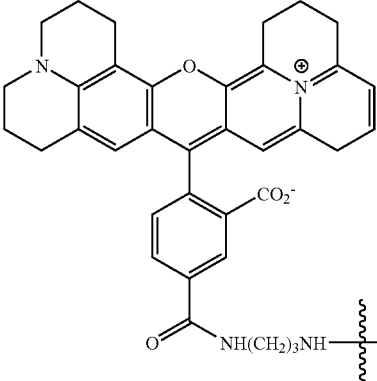

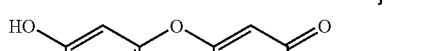

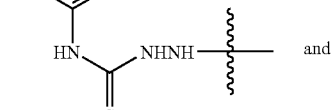

and

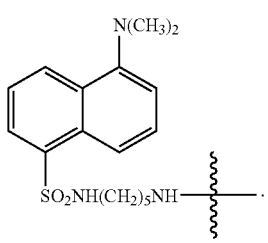

Further, $R_7$ may be selected from the group consisting of H, alkyl and aryl.

Also within formula (I), $R_1$ and $R_3$ may each independently be selected from the group consisting of H, alkyl, aryl and an amine protecting group; $R_2$ may be selected from the group consisting of H, aryl, alkyl, —$CO_2W$, wherein W is H, alkyl, aryl or a carboxylic acid protecting group, and

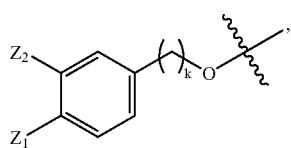

wherein $Z_1$ and $Z_2$ are each independently selected from the group consisting of H, —OH, —$NH_2$, —$NHCH_3$ and —$CO_2H$; and $R_4$ may equal

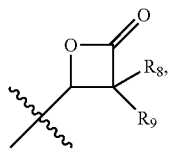

wherein $R_8$ and $R_9$ may each independently be selected from the group consisting of H, alkyl, aryl, —CH(OH)alkyl, —CH(OH)aryl, —$OR_{10}$ and —$NR_{11}R_{12}$, wherein $R_{10}$-$R_{12}$ may each independently be selected from the group consisting of H, alkyl, aryl, acetyl, —$SiR_{13}R_{14}R_{15}$, an alcohol protecting group and an amine protecting group, wherein $R_{13}$-$R_{15}$ may each independently be selected from the group consisting of alkyl and aryl; and n may equal 1-7 (e.g., 1, 2, 3, 4, 5, 6, or 7, or any range derivable therein), depending on the need for greater chain length, flexibility and/or distance between the two termini of the overall compound.

When a compound of formula (I) is contemplated, provisos such as the following may apply: if $R_0$ equals

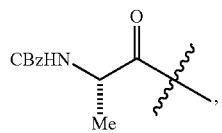

$R_2$ equals Bn and n equals 3, then $R_4$ cannot be

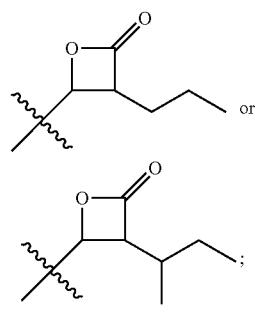

and if $R_0$ equals

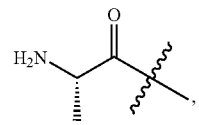

$R_2$ equals H and n equals 3, then $R_4$ cannot be

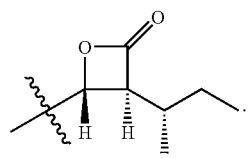

In certain preferred embodiments of the compound comprising formula (I), Ro equals H and $R_1$ equals an amine protecting group.

In other preferred embodiments, $R_0$ equals

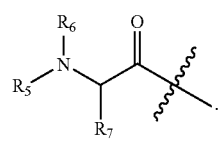

When $R_0$ is so chosen, $R_5$ is, in certain preferred embodiments, an amine protecting group. When $R_0$ is so chosen, $R_6$ is preferably H. When $R_0$ is so chosen, $R_7$ is preferably —$CH_3$. In another preferred embodiment, $R_5$ is an amine protecting group, $R_6$ is H and $R_7$ is —$CH_3$. The amine protecting group may be Cbz, in certain embodiments. In other preferred embodiments, $R_7$ is —$CH_3$ and $R_5$ is

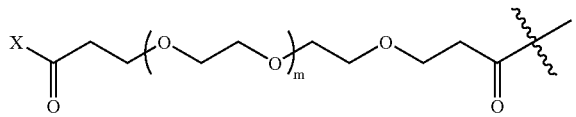

wherein, in certain preferred embodiments, m is 1 and wherein, in certain preferred embodiments, X is

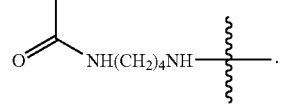

In other preferred embodiments of the compound comprising formula (I), $R_1$ is H. In certain embodiments, $R_2$ is alkyl and in certain other embodiments, $R_2$ is a carboxylic acid or a protected carboxylic acid. The protected carboxylic acid may, in certain embodiments, be protected by a benzyl protecting group. In certain embodiments, R₃ is H. In certain embodiments, R₄ is

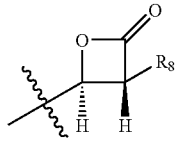

and in other certain embodiments, R₄ is

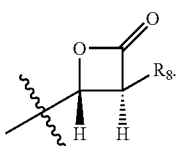

In some preferred embodiments, either R₈ or R₉ is H, whereas in other preferred embodiments, R₈ is —OR₁₀ and R₉ is H. R₁₀ may be, in certain preferred embodiments, selected from the group consisting of H, an alcohol protecting group and —SR₁₃R₁₄R₁₅. R₁₃-R₁₅ may independently be, in certain embodiments, H, alky or aryl, with ethyl groups comprising a preferred embodiment. In certain embodiments, R₈ is either alkyl or aryl and R₉ is H. In certain embodiments, R₈ is —CH(OH)alkyl or —CH(OH)aryl and R₉ is H. R₈ may be phenyl, in certain embodiments, and may be substituted with any of the substituents as described herein. In certain embodiments, R₈ is —NR₁₁R₁₂ and R₉ is H. R₁₁ and R₁₂ may each independently be selected from the group consisting of H, acetyl and an amine protecting group, in preferred embodiments. Preferably, n equals 1-5 (e.g., 1, 2, 3, 4, or 5, or any range derivable therein), and even more preferably, n equals 3.

In certain embodiments, a compound of the following formula is contemplated:

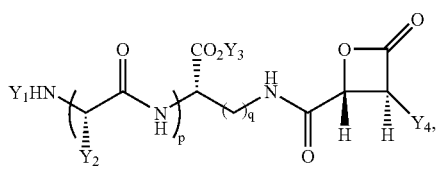

wherein: Y₁ is selected from the group consisting of H, Cbz, Fmoc, PMB, BOM and

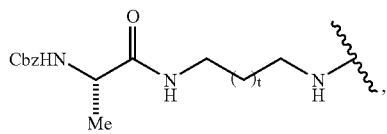

wherein t is 1-2; Y₂ is H or —CH₃; Y₃ is selected from the group consisting of H, Bn,

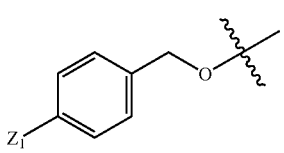

and

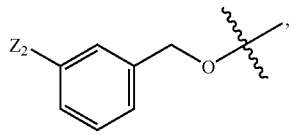

wherein Z₁ and Z₂ are each independently selected from the group consisting of H, —OH, —NH₂, —NHCH₃ and —CO₂H; Y₄ is selected from the group consisting of —CH₃, —C₆H₁₃, —CH₂Cy, —CH(OH)Cy, phenyl, —CH₂C₆H₅ and —CH(OH)C₆H₅; p is 0 or 1; and q is 1-5 (e.g., 1, 2, 3, 4, or 5, or any range derivable therein).

In certain embodiments, a compound of the following formula is contemplated:

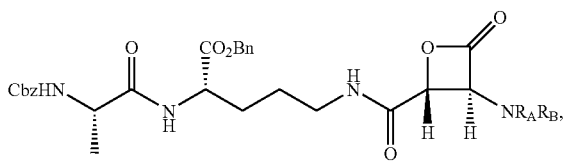

wherein R_A is selected from the group consisting of H, Bn and PMB and R_B is selected from the group consisting of H, Bn, PMB, —C(O)CH₃, Cbz and Boc.

In certain embodiments, a compound of the following formula is contemplated:

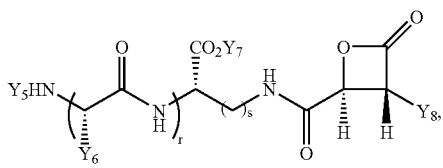

wherein:

Y₅ is selected from the group consisting of H, Cbz, Fmoc, PMB, BOM and

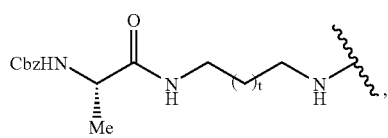

wherein t is 1-2; Y₆ is H or —CH₃; Y₇ is selected from the group consisting of H, Bn,

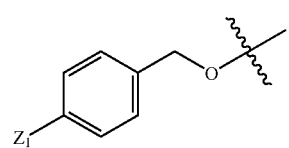

and

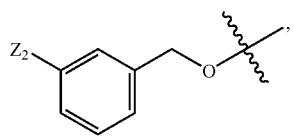

wherein $Z_1$ and $Z_2$ are each independently selected from the group consisting of H, —OH, —NH$_2$, —NHCH$_3$ and —CO$_2$H; $Y_8$ is selected from the group consisting of —CH$_3$, —C$_6$H$_{13}$, —CH$_2$Cy, —CH(OH)Cy, phenyl, —CH$_2$C$_6$H$_5$ and —CH(OH)C$_6$H$_5$; r is 0 or 1; and s is 1-5 (e.g., 1, 2, 3, 4, or 5, or any range derivable therein).

In certain embodiments, a compound of the following formula is contemplated:

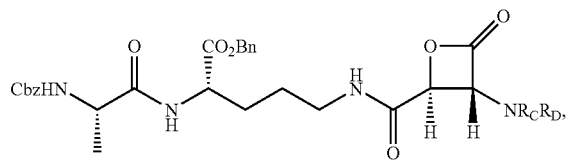

wherein $R_C$ is selected from the group consisting of H, Bn and PMB and $R_D$ is selected from the group consisting of H, Bn, PMB, —C(O)CH$_3$, Cbz and Boc.

In specific embodiments, the following compound is contemplated:

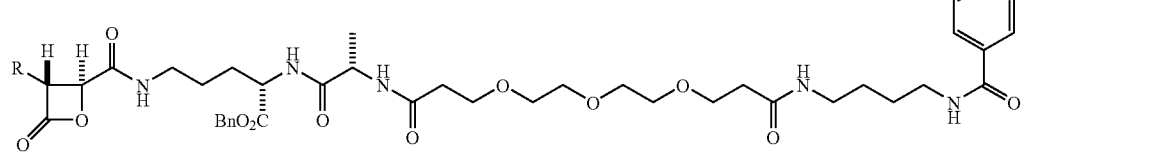

In specific embodiments, the following compound is contemplated:

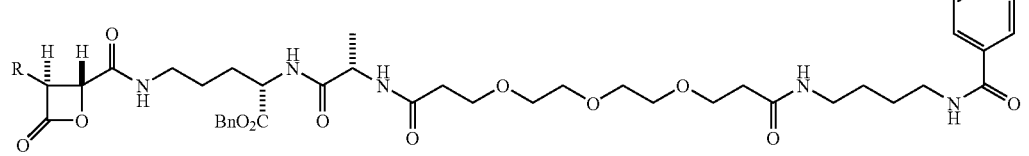

Another general aspect of the present invention contemplates a method of synthesizing a compound of formula (I):

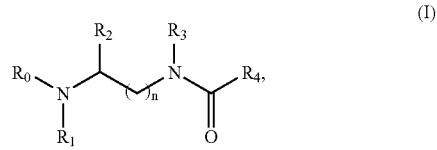

comprising obtaining a first compound of formula (II):

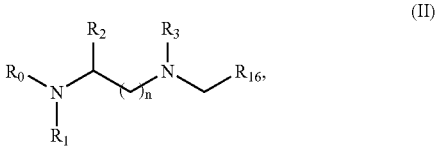

and admixing it with a second compound of formula (III) or (IV):

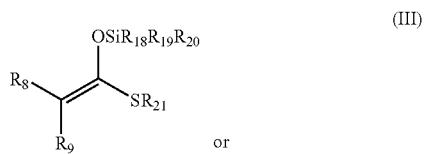

-continued

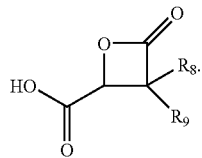

(IV)

Preparations of these compounds may be by any method known to those of skill in the art, and exemplary methods are described herein. The first compound may comprise, for example, a dipeptide or a tripeptide.

When a compound of formula (III) is chosen as the second compound, the reaction conditions may comprise, in certain embodiments, a Lewis acid. Lewis acids are well-known to those of skill in the art. Non-limiting examples of Lewis acids include $ZnCl_2$, $Zn(OTf)_2$ and $5 nCl_4$. A chosen solvent for this reaction may comprise any type as described herein and in preferred embodiments, the solvent is methylene chloride. Reaction conditions typically take place at room temperature for periods of 8-36 hours, with 12-24 hours being more preferable. Reactions may be monitored by any means known to those of skill in the art, such as thin-layer chromatography and HPLC. Purification can take place via any means known to those of skill in the art, with silica gel column chromatography comprising a preferred embodiment.

Within formula (III) or (IV), $R_8$ and $R_9$ may each independently be selected from the group consisting of H, alkyl, aryl, —CH(OH)alkyl, —CH(OH)aryl, —$OR_{22}$ and —$NR_{23}R_{24}$, wherein $R_{22}$-$R_{24}$ may each independently be selected from the group consisting of H, alkyl, aryl, acetyl, —$SiR_{25}R_{26}R_{27}$, an alcohol protecting group and an amine protecting group, wherein $R_{25}$-$R_{27}$ may each independently be selected from the group consisting of H, alkyl and aryl; and n may equal 1-7, depending on the need or wish for greater chain length, flexibility and/or distance between the two termini of the overall compound. In certain preferred embodiments, $R_{25}$-$R_{27}$ are each ethyl. $R_{18}$-$R_{20}$ may comprise, independently, H, alkyl or aryl, with ethyl groups being more preferred. $R_{21}$ may comprise, in some embodiments, H, alkyl or aryl, with aryl groups being preferable, and pyridyl and phenyl groups being more preferable, and pyridyl groups being even more preferable.

When a compound of formula (IV) is chosen as the second compound, the reaction conditions may comprise a coupling agent, as described herein. A chosen solvent for this reaction may comprise any type described herein and in preferred embodiments, the solvent comprises ethyl acetate/water. Reaction conditions typically take place at room temperature for periods under 24 hours. Reactions may be monitored by any means known to those of skill in the art, such as thin-layer chromatography and HPLC. Purification can take place via any means known to those of skill in the art, with silica gel column chromatography comprising a preferred embodiment.

When employing this method, $R_0$ may be selected from the group consisting of H, alkyl, an amine protecting group and

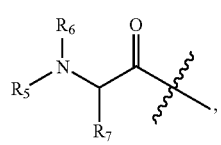

wherein $R_5$ and $R_6$ may each independently be selected from the group consisting of H, alkyl, aryl, an amine protecting group and

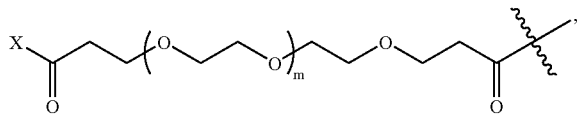

wherein m may range in length from 1-5, depending on the desired length of this flexible linker, and X may comprise a fluorophore as described herein. In preferred embodiments, the fluorophore may be selected from the group consisting of:

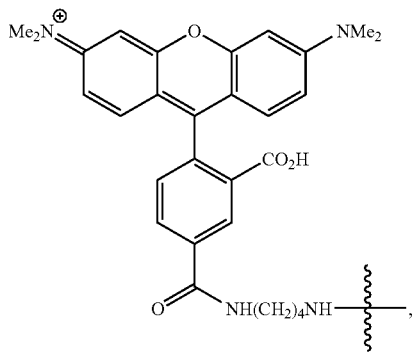

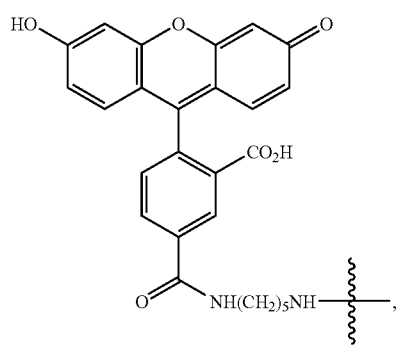

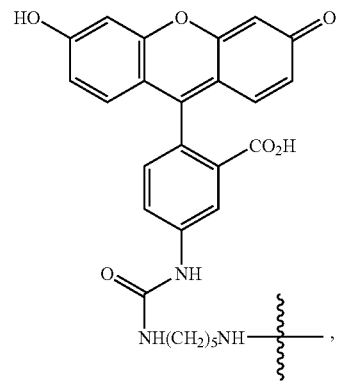

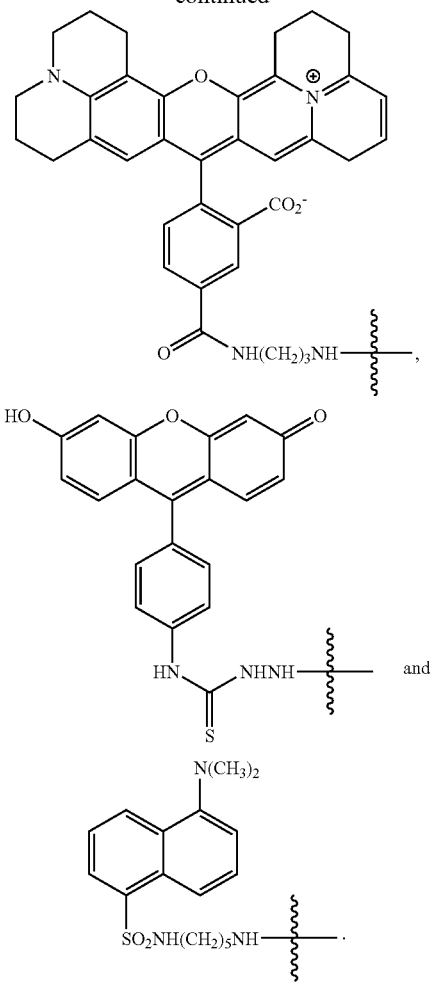

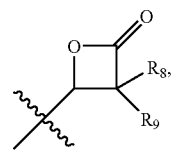

wherein $R_8$ and $R_9$ may be as described above.

In certain preferred embodiments of this method, $R_0$ equals H and $R_1$ equals an amine protecting group, such as Cbz. In other preferred embodiments, $R_0$ equals

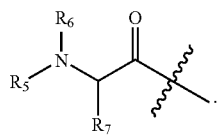

In certain embodiments, $R_5$ is an amine protecting group. In certain embodiments, $R_6$ is H. In certain embodiments, $R_7$ is $CH_3$. In a certain preferred embodiment, $R_5$ is an amine protecting group, $R_6$ is H and $R_7$ is $CH_3$. The amine protecting group may be, in certain embodiments, Cbz. In some preferred embodiments, $R_7$ is $CH_3$ and $R_5$ is

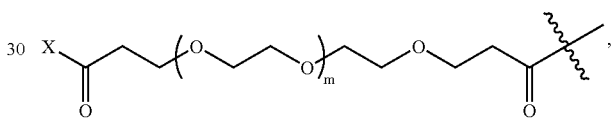

or any other linker or spacer known to those of skill in the art. In certain preferred embodiments, m is 1. In certain preferred embodiments, X is

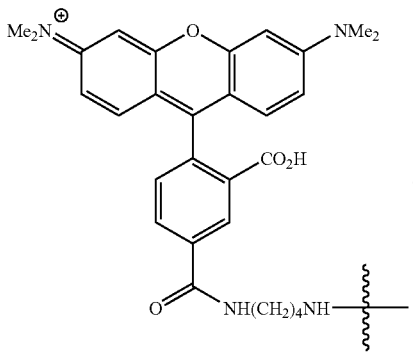

In certain preferred embodiments, $R_1$ is H. In certain preferred embodiments, $R_2$ is alkyl and in other preferred embodiments, $R_2$ is a carboxylic acid protecting group, such as Bn. In certain preferred embodiments, $R_3$ is H.

In certain embodiments of the method, the $R_4$ group generated by this method comprises

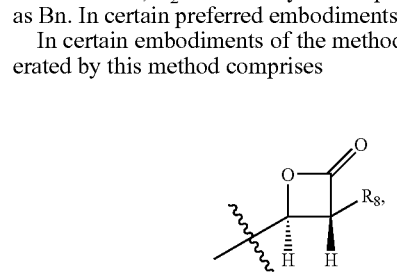

Further, $R_7$ may be selected from the group consisting of H, alkyl and aryl.

Also within this method, $R_1$ and $R_3$ may each independently be selected from the group consisting of H, alkyl, aryl and an amine protecting group; and $R_2$ may be selected from the group consisting of H, aryl, alkyl, —$CO_2W$, wherein W is H, alkyl, aryl or a carboxylic acid protecting group, and

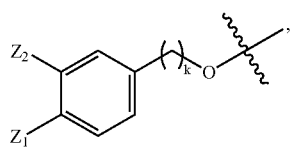

wherein $Z_1$ and $Z_2$ are each independently selected from the group consisting of H, —OH, —$NH_2$, —$NHCH_3$ and —$CO_2H$. $R_{16}$ may be selected from the group consisting of H, —C(O)CHO and —C(O)C(O)$R_{17}$, wherein $R_{17}$ may be selected from the group consisting of alkyl and aryl. The chain length represented by n may range from 1-7, depending on the need or wish for greater chain length, flexibility and/or distance between the two termini of the overall compound. Further, $R_4$, as generated via this method, may equal whereas in other embodiments, the $R_4$ group generated by this method comprises

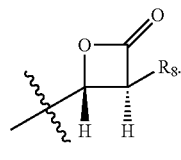

In certain preferred embodiments of this method, either $R_8$ or $R_9$ is H. In other preferred embodiments, $R_8$ is either alkyl or aryl and $R_9$ is H. In other preferred embodiments, $R_8$ is —$OR_{10}$ and $R_9$ is H. In certain embodiments, $R_8$ is —CH(OH)alkyl or —CH(OH)aryl and $R_9$ is H. In certain preferred embodiments, $R_{10}$ is selected from the group consisting of H, an alcohol protecting group and $SR_{13}R_{14}R_{15}$. $R_{13}$-$R_{15}$ may comprise, for example, H, alkyl or aryl, with ethyl groups being more preferred. In certain preferred embodiments, $R_8$ is phenyl. In other preferred embodiments, $R_8$ is —$NR_{11}R_{12}$ and $R_9$ is H. $R_{11}$, and $R_{12}$, in preferred embodiments, may each independently be selected from the group consisting of H, acetyl and an amine protecting group.

Another preferred embodiment of this method contemplates n equaling 1-5, with n equaling 3 being a more preferred embodiment. Yet another preferred embodiment comprises $R_{17}$ as Bn.

When employing the method of the present invention, provisos such as the following may apply: when formula (II) comprises

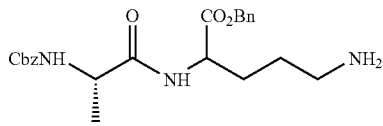

and is reacted with a compound of Formula (IV), then in the structure of Formula (IV), $R_8$ and $R_9$ together may not be H and propyl, respectively, or H and 2-methylpropyl, respectively.

In certain methods of the present invention, a compound of formula (XI) is formed as an intermediate:

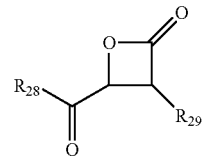

wherein $R_{28}$ is —OH or

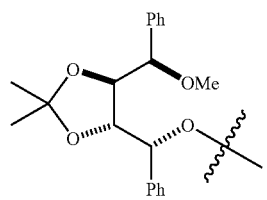

and $R_{29}$ is selected from the group consisting of H, alkyl, aryl, —$CH_2Cy$, —CH(OH)alkyl, —CH(OH)aryl, —$OR_{22}$ and —$NR_{23}R_{24}$, wherein $R_{22}$-$R_{24}$ are each independently selected from the group consisting of H, alkyl, aryl, acetyl, —$SiR_{25}R_{26}R_{27}$, an alcohol protecting group and an amine protecting group, wherein $R_{25}$-$R_{27}$ are each independently selected from the group consisting of alkyl and aryl; and optical isomers thereof.

It is specifically contemplated that in certain embodiments, compounds disclosed in WO 00/043000 and/or U.S. Pat. No. 7,223,745 are not encompassed by the present invention. Compounds disclosed in Arionov and De Meijere, 2004, are also excluded, in certain embodiments. Each of these three references are specifically incorporated herein in their entireties. For example, the following compounds may be excluded, in certain embodiments:

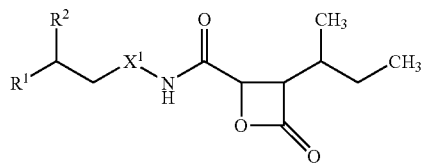

| Compound No. | $R^1$ | $R^2$ | $X^1$ |
|---|---|---|---|
| 44 | 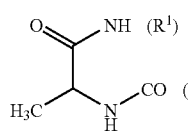 | | |
| 45 | | 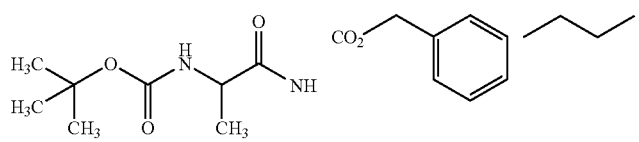 | |

-continued
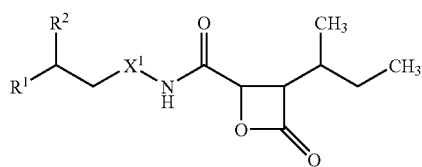
| Compound No. | R¹ | R² | X¹ |
|---|---|---|---|
| 46* | 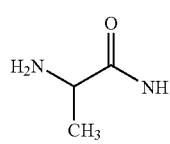 | 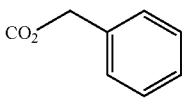 | ~~~ |
*CF₃CO₂H salt
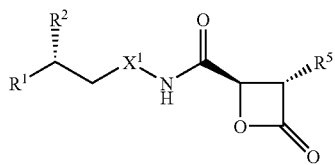
| Compound No. | R¹ | R² | R⁵ | X¹ |
|---|---|---|---|---|
| 47 | 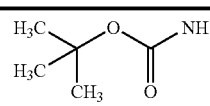 | 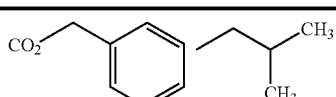 | | linkage |
| 48 | 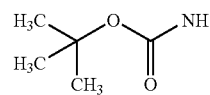 | 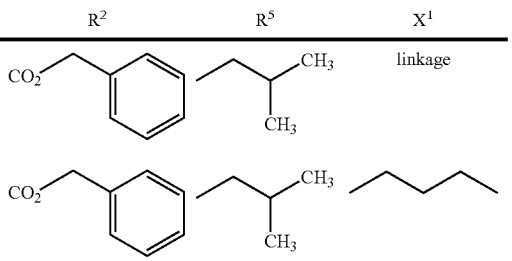 | | ~~~ |
| 49 | 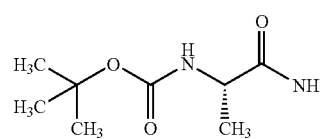 | 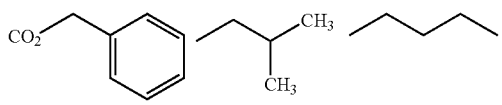 | | ~~~ |
| 50* | 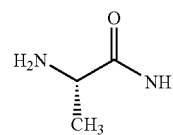 | 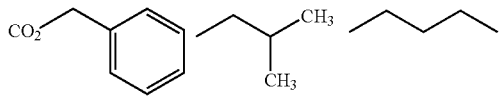 | | ~~~ |
| 51 | 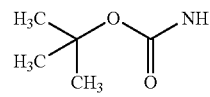 | H | 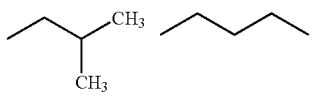 | ~~~ |
| 52* | H₂N | H | 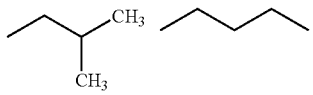 | ~~~ |
| 53 | 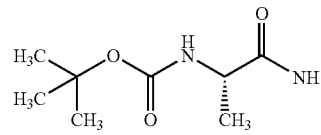 | H | 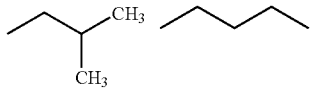 | ~~~ |
*CF₃CO₂H salt

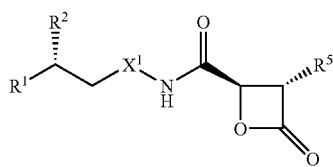
| Compound No. | R¹ | R² | R⁵ | X¹ |
|---|---|---|---|---|
| 54 | 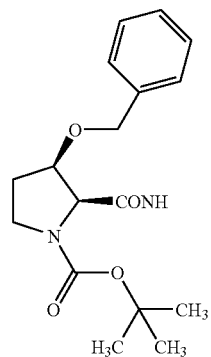 | H | 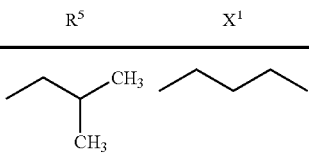 |  |
| 55 | H | 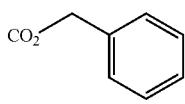 | 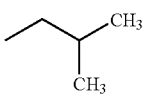 |  |
| 56 | 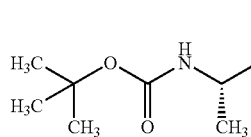 | 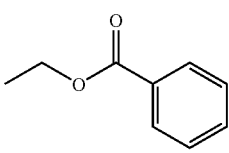 | 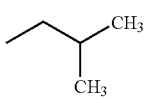 | 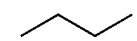 |
| 57 | 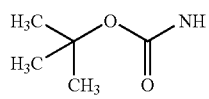 | CO₂H | 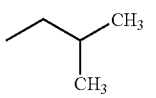 | 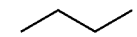 |
| 58 | 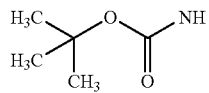 | 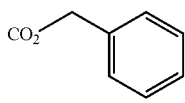 | 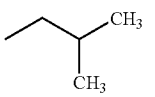 | 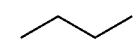 |
| 59 | 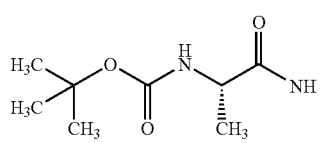 | 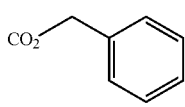 | 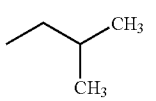 | 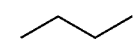 |
| 60* | 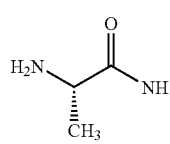 | 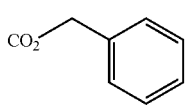 | 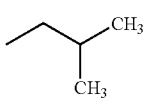 | |
*CF₃CO₂H salt

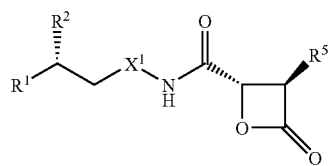

| Compound No. | R¹ | R² | R⁵ | X¹ |
|---|---|---|---|---|
| 61 | H₃C-C(CH₃)₂-O-C(O)-NH- | -CO₂-CH₂-C₆H₅ | -CH₂CH(CH₃)₂ | -(CH₂)₄- |
| 62* | H₂N- | -CO₂-CH₂-C₆H₅ | -CH₂CH(CH₃)₂ | -(CH₂)₄- |
| 63 | H₃C-C(CH₃)₂-O-C(O)-NH-CH(CH₃)-C(O)-NH- | -CO₂-CH₂-C₆H₅ | -CH₂CH(CH₃)₂ | -(CH₂)₄- |
| 64* | H₂N-CH(CH₃)-C(O)-NH- | -CO₂-CH₂-C₆H₅ | -CH₂CH(CH₃)₂ | -(CH₂)₄- |
| 65 | H₃C-C(CH₃)₂-O-C(O)-NH- | H | -CH(CH₃)CH₂CH₃ | -(CH₂)₄- |
| 66* | H₂N- | H | -CH(CH₃)CH₂CH₃ | -(CH₂)₄- |

*CF₃CO₂H salt

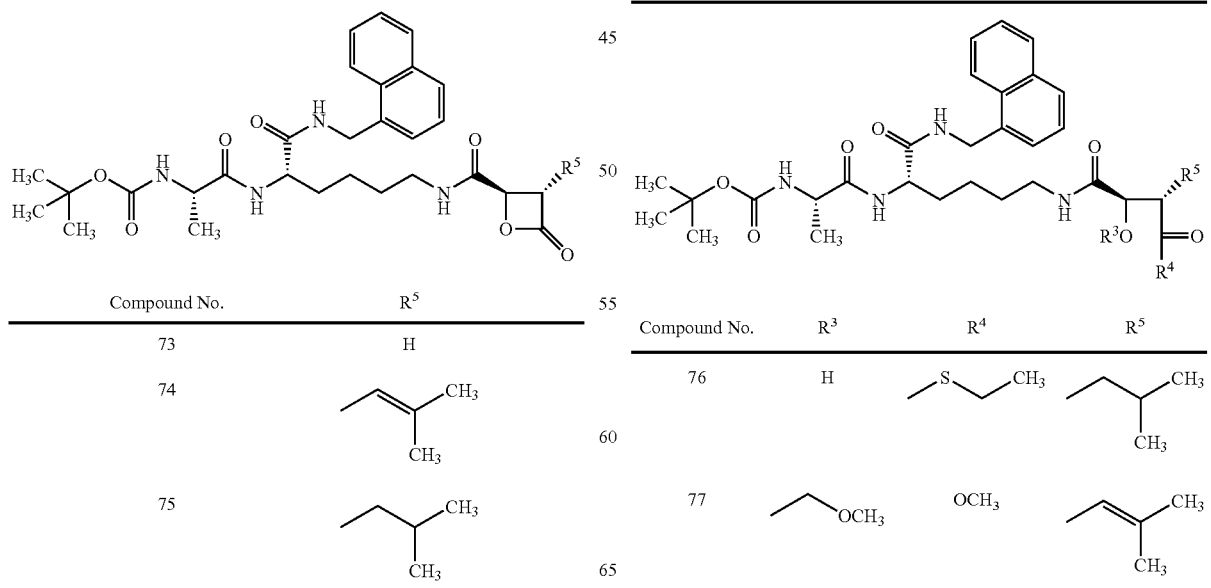

| Compound No. | R⁵ |
|---|---|
| 73 | H |
| 74 | -CH=C(CH₃)₂ |
| 75 | -CH(CH₃)CH₂CH₃ |

| Compound No. | R³ | R⁴ | R⁵ |
|---|---|---|---|
| 76 | H | -S-CH₂CH₃ | -CH₂CH(CH₃)₂ |
| 77 | -CH₂-OCH₃ | -OCH₃ | -CH=C(CH₃)₂ |

-continued

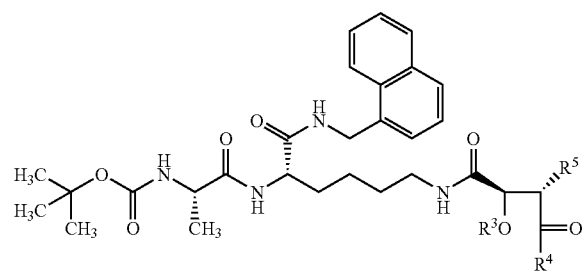

| Compound No. | R³ | R⁴ | R⁵ |
|---|---|---|---|
| 78 | CH₃CH₂OCH₃ (ethoxymethyl) | OCH₃ | CH(CH₃)CH₂CH₃ |
| 79 | CH₃CH₂OCH₃ (ethoxymethyl) | OH | CH(CH₃)CH₂CH₃ |

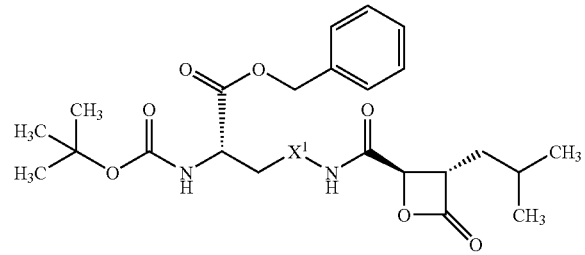

Compound No.    X¹

80  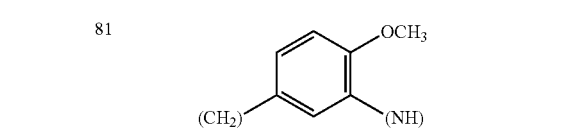

81

82

71  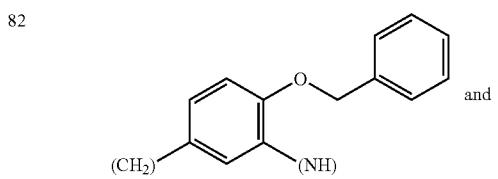

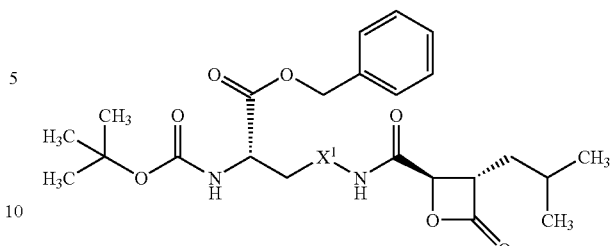

Compound No.    X¹

72  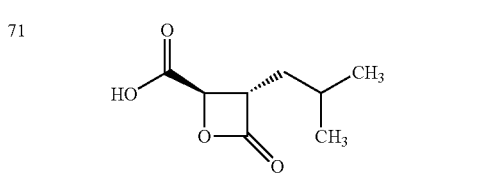, as well as

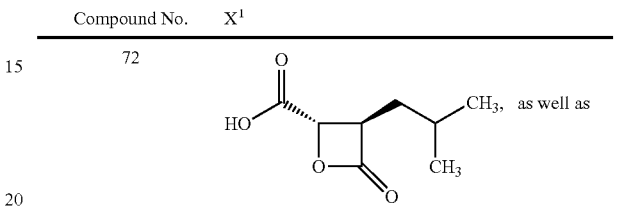 and

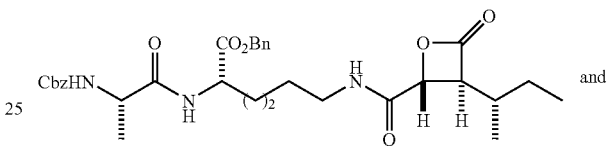

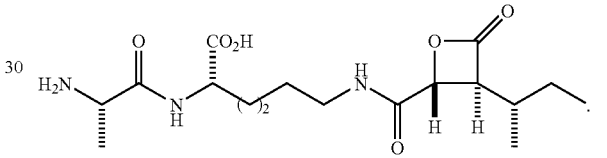

Certain aspects of the present invention contemplate a method of inhibiting the 20S proteasome, comprising contacting a cell with an effective amount of a compound as described herein. One skilled in the art can purify and measure the activity of the proteasome using approaches such as those described in the following citations: Hirano et al., 2005; Akaishi et al., 1996; Ugai et al., 1993; Adams et al., 1999; and Mellgren, 1997, each of which is incorporated herein by reference in its entirety. The method may take place in vitro or in vivo. Compounds of the present invention may also be used to treat proteasome-related conditions, such as cancer, Alzheimer's disease, malaria, tuberculosis, eye disorders and asthma. Accordingly, methods of treatment of these conditions are also contemplated. Compounds used in these methods may be comprised in a pharmaceutically acceptable excipient, diluent, or vehicle.

Certain aspects of the present invention contemplate a method of inhibiting fatty acid synthase, comprising contacting a cell with an effective amount of a compound as described herein. For example, compounds may be screened for their ability to inhibit the thioesterase domain of fatty acid synthase, which liberates palmitate, the natural substrate, from the enzyme. One of ordinary skill in the art could express and purify the recombinant thioesterase using procedures described in, e.g., Chakravarty et al., 2004 and Kridel et al., 2004. In this study the thioesterase domain of fatty acid synthase was PCR amplified using the following primers: 5_ATG ACG CCC AAG GAG GAT GGT CTG GCC CAG CAG (corresponds to nucleotides 6727-6756) and 3_GCC CTC CCG CAC GCT CAC GCG TGG CT (corresponds to nucleotides 7625-7650). The recombinant thioesterase domain was cloned into pTrcHis (Invitrogen) and expressed in *Escheria coli*. The recombinant protein corresponds to residues 2202 through 2509 of FAS. The thioesterase was purified by Ni-affinity chromatography. The method may take place in vitro or in vivo. Compounds of the present invention may also be used to treat fatty acid-synthase-related conditions, which generally includes diseases characterized by hyperproliferation of cells such as inflammation, angiogenesis and cancer. Such compounds may also be of use in treating obesity as fatty acid synthase is the only enzyme that converts dietary carbohydrate to fat. Accordingly, methods of treatment of these conditions are also contemplated. Compounds used in these methods may be comprised in a pharmaceutically acceptable excipient, diluent, or vehicle. The inhibition of fatty acid synthase in cells can be measured by, for example, directly determining the amount of palmitate synthesized by the cell using methods described in Browne et al., 2006, Kridel et al., 2004 and Pizer et al., 1996.

Another general aspect of the present invention contemplates a method of treating cancer comprising administering to a subject an effective amount of a compound as described herein. The subject may be a mammal, such as a human. The cancer may be any cancer treatable by administration of a compound described herein. For example, the cancer may be breast, prostate, ovarian, brain hepatocarcinoma, melanoma, colorectal, liver, lymphoma, lung, oral, head, neck, spleen, lymph node, small intestine, large intestine, blood cells, stomach, endometrium, testicle, skin, esophagus, bone marrow, blood, cervical, bladder, Ewing's sarcoma, thyroid, and/or gastrointestinal.

The terms "inhibiting," "reducing," or "prevention," or any variation of these terms, when used in the claims and/or the specification includes any measurable decrease or complete inhibition to achieve a desired result.

The term "contact," when applied to a cell, is used herein to describe the process by which a compound of the invention is delivered to a target cell or is placed in direct juxtaposition with the target cell.

As used herein, the term "effective" (e.g., "an effective amount") means adequate to accomplish a desired, expected, or intended result. For example, an "effective amount" may be an amount of a compound sufficient to produce a therapeutic benefit (e.g., effective to reproducibly inhibit decrease, reduce, inhibit or otherwise abrogate the growth of a cancer cell). "Effective amounts" or a "therapeutically relevant amount" are those amounts of a compound sufficient to produce a therapeutic benefit (e.g., effective to reproducibly inhibit decrease, reduce, inhibit or otherwise abrogate the growth of a cancer cell). An effective amount, in the context of treating a subject, is sufficient to produce a therapeutic benefit. The term "therapeutic benefit" as used herein refers to anything that promotes or enhances the well-being of the subject with respect to the medical treatment of the subject's condition.

As used herein, a "suitable solvent" or a "chosen solvent" is a solvent that will facilitate, or at least not significantly impede, the reaction that takes place within that solvent. A suitable solvent choice may depend on, for example, which one(s) will facilitate the solubilizing of all the reagents, or, for example, which one(s) will best facilitate the desired reaction (particularly if the mechanism of the reaction is known). However, a suitable solvent need not completely solubilize each reagent and may actually impede the desired reaction to some degree. Suitable solvents for the methods of the present invention will be known to one of ordinary skill in the art. More than one solvent may be chosen for any particular reaction. Water may also be admixed into any solvent choice, particularly when improvements in solubility of the reagents are required. Suitable solvents may include, for example, polar solvents and non-polar solvents. Suitable solvents include, but are not limited to, dimethylformamide, dimethylsulfoxide, dioxane, methanol, ethanol, hexane, ethyl acetate, methylene chloride, tetrahydrofuran and acetonitrile. In some preferred embodiments, suitable solvents include methylene chloride, tetrahydrofuran and ethyl acetate/water.

As used herein a "coupling agent" is a reagent used to facilitate the coupling of two compounds. In preferred embodiments, a coupling agent facilitates the coupling of an $NH_2$-containing compound with a —$CO_2H$-containing compound to form an amide bond between the two compounds. Coupling agents are well known to those of ordinary skill in the art and may be employed in certain embodiments of methods of the present invention. Examples of coupling agents include, but are not limited to, 1-ethyl-3-(3-dimethylaminopropyl) carbodiimide (EDAC) and dicyclohexylcarbodiimide (DCC), optionally in conjunction with catalytic amounts of dimethylaminopyridine (DMAP) as a promoter. Other carbodiimides are also envisioned as coupling agents. Coupling agents are discussed, for example, in Bodansky, 1993 and Grant, 1992. These coupling agents may be used singly or in combination with each other or other agents to facilitate conjugation. Once the two substrates are conjugated using coupling agents, a urea by-product is typically formed. The urea by-product may be removed by filtration. The conjugated product may then be purified by, for example, silica gel column chromatography or HPLC.

As used herein, a "chiral auxiliary" refers to an easily removable chiral group that is capable of influencing the direction of nucleophilic attack. Chiral auxiliaries typically control the diastereoselectivity of a reaction. Persons of skill in the art are familiar with such compounds, and many are commercially available.

Known and unknown equivalents of the specific compounds, agents, and active ingredients discussed throughout this specification can be used with the compositions and methods of the present invention. The equivalents can be used as substitutes for the specific compounds, agents, and active components. The equivalents can also be used to add to the methods and compositions of the present invention. A person of ordinary skill in the art would be able to recognize and identify acceptable known and unknown equivalents to the specific compounds, agents, and active ingredients without undue experimentation.

Persons of ordinary skill in the art will be familiar with methods of purifying compounds of the present invention. One of ordinary skill in the art will understand that compounds of the present invention can generally be purified at any step, including the purification of intermediates as well as purification of the final products. In certain embodiments of the present invention, purification of a compound does not remove all impurities. In some embodiments, such impurities can be identified. Non-limiting examples of purification methods include gel filtration, size exclusion chromatography (also called gel filtration chromatography, gel permeation chromatography or molecular exclusion), dialysis, distillation, crystallization, recrystallization, reprecipitation, sublimation, electrophoresis, prep thin-layer chromatography, silica gel column chromatography and high-performance liquid chromatography (HPLC), including normal-phase HPLC and reverse-phase HPLC. In preferred embodiments, purification comprises silica gel column chromatography.

Methods of determining the purity of compounds are well known to those of skill in the art and include, in non-limiting examples, autoradiography, mass spectroscopy, melting point determination, ultra violet analysis, calorimetric analysis, (HPLC), thin-layer chromatography and nuclear magnetic resonance (NMR) analysis (including, but not limited to, $^1$H and $^{13}$C NMR). In preferred embodiments, purity is determined via NMR. Software available on various instruments (e.g., spectrophotometers, HPLCs, NMRs) can aid one of skill in the art in making these determinations, as well as other means known to those of skill in the art.

Prodrugs and solvates of the compounds of the present invention are also contemplated herein. Any compound described herein may be a prodrug. The term "prodrug" as used herein, is understood as being a compound which, upon administration to a subject, such as a mammal, undergoes chemical conversion by metabolic or chemical processes to yield a compound any of the formulas herein, or a salt and/or solvate thereof (Bundgaard, 1991; Bundgaard, 1985). Solvates of the compounds of the present invention are preferably hydrates.

As used herein, "predominantly one enantiomer" or "substantially free" from other optical isomers means that the compound contains at least about 95% of one enantiomer, or more preferably at least about 98% of one enantiomer, or most preferably at least about 99% of one enantiomer. Any compound described herein may, in certain embodiments, be present as predominantly one enantiomer.

In certain embodiments, "substantially pure" compounds are contemplated. That is, any compound as described herein may be a substantially pure compound. As used herein, the term "substantially pure" refers to compounds that are at least about 95% pure, or more preferably at least about 98% pure, or most preferably at least about 99% pure.

It is contemplated that any embodiment discussed in this specification can be implemented with respect to any method, compound or composition of the invention, and vice versa. Furthermore, compounds and compositions of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects. For example, "about" can be within 10%, preferably within 5%, more preferably within 1%, and most preferably within 0.5%.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DESCRIPTION OF ILLUSTRATIVE EMBODIMENTS

Figure 1:
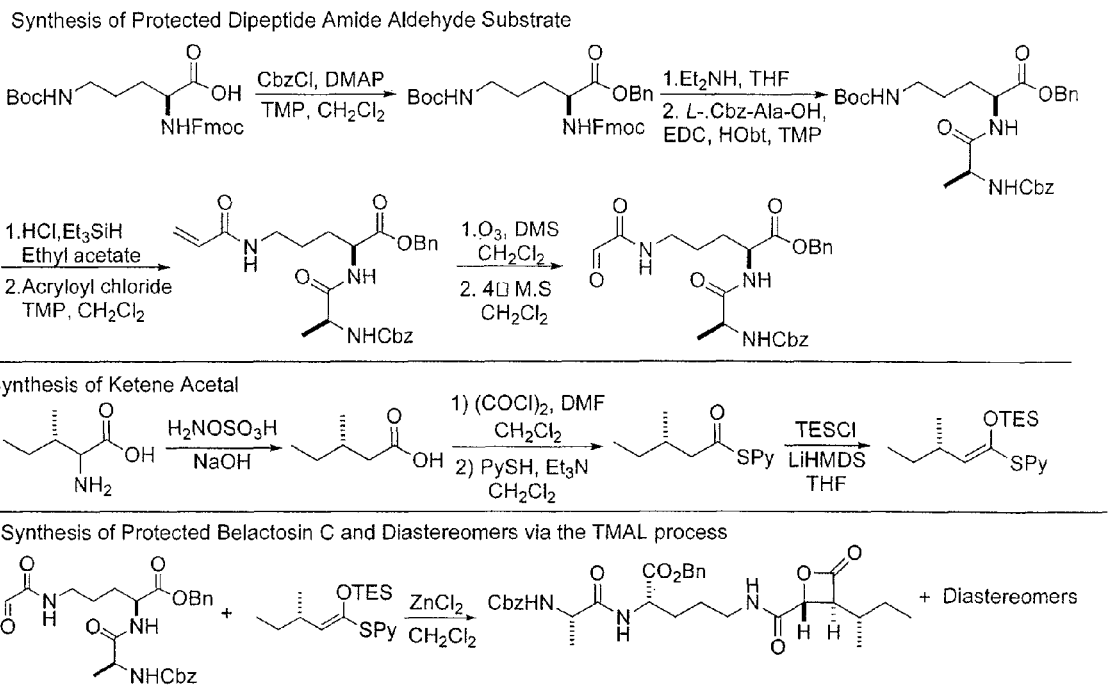
FIG. 1. General synthetic method for belactosin C and derivatives: Synthesis of aldehyde dipeptide and direct synthesis of belactosin via the tandem Mukaiyama aldol lactonization (TMAL) process. Note: 4 □ M. S=4 Å molecular sieves.

The present invention overcomes the deficiencies of the prior art by providing novel derivatives of belactosin as well as a facile means of synthesizing said derivatives. As discussed above, belactosin and its derivatives feature a beta-lactone ring, and this moiety is pivotal for bioactivity. Kumaraswamy et al., 2006. In some embodiments, belactosin derivatives of the present invention may function as inhibitors of human fatty acid synthase (FAS) and/or the proteasome. Since some proteasome inhibitors represent potential novel anticancer therapy, synthetic derivatives of belactosin featuring the beta-lactone moiety are potential therapeutic targets of the proteasome. Adams et al., 2000; Murray et al., 2000; Adams et al., 1999; Adams et al., 2002a; Adams et al., 2002b.

Orlistat, a drug approved for treating obesity, also features a beta-lactone ring moiety. Purohit et al., 2006; Kridel et al., 2004; Knowles et al., 2004. This drug has recently been shown to be a potent inhibitor of FAS; further, this natural product derivative is cytotoxic and cytostatic to tumor cells in vitro and can inhibit tumor growth in vivo. Kridel et al., 2004; Knowles et al., 2004. FAS is responsible for the cellular synthesis of palmitate and is attracting great interest as a drug target in oncology because it is up-regulated in most solid tumors, including those of the breast, prostate and ovary. Purohit et al., 2006; Alo et al., 1996; Swinnen et al., 2002; Rossi et al., 2003; Pizer et al., 1996a; Pizer et al., 1996b; Pizer et al., 2000; Pizer et al., 2001; Gansler et al., 1997. Furthermore, a number of studies show that a pharmacologic blockade of FAS can be cytostatic and cytotoxic to tumor cells. Kuhajda et al., 2000; Kuhajda et al., 1994; Pizer et al., 1998; Funabashi et al. 1989; Pizer et al., 2000.

Beta-lactone inhibitors of FAS typically function by acylating the active site serine residue, leading to inhibition of thioesterase (TE) activity and ultimately apoptosis—that is, cell death. Purohit et al., 2006. Similarly, beta-lactone inhibitors of the proteasome typically function by acylation of the active site threonine (chymotrypsin activity of the proteasome). Simon et al., 2006; Maier et al., 2006. Compounds of the present invention, which typically comprise beta-lactone moieties similar to those found in such agents as the belactosins and orlistat, are capable, in certain embodiments, of acylating the active site serine of the FAS-TE and also the threonine of the proteasome, thus typically leading to dual inhibition. Accordingly, in certain embodiments, compounds of the present invention are attractive anti-cancer agents for study. Such compounds may also be useful for as substrates for other proteins (e.g., enzymes) which recognize the beta-lactone moiety.

Further, a facile means of accessing compounds of the present invention comprises, in preferred embodiments, a tandem Mukaiyama aldol lactonization (TMAL) reaction. The synthetic methodology of the present invention offers, in certain embodiments, access to these biologically interesting beta-lactones in fewer steps than many methodologies previously attempted. Moreover, any compound comprising a beta-lactone moiety may be prepared using methods disclosed herein.

1. Chemical Definitions

The term "alkyl" includes straight-chain alkyl, branched chain alkyl, cycloalkyl (Cy) (alicyclic), cyclic alkyl (e.g., —CH$_2$-cyclopropyl), heteroatom-unsubstituted alkyl, heteroatom-substituted alkyl, heteroatom-unsubstituted C$_n$-alkyl, and heteroatom-substituted C$_n$-alkyl. Alkyl groups may also optionally contain alkene or alkyne C—C bonds (but not such that aromatic compounds result). In certain embodiments, lower alkyls are contemplated. The term "lower alkyl" refers to alkyls of 1-6 carbon atoms (that is, 1, 2, 3, 4, 5 or 6 carbon atoms). The term "heteroatom-unsubstituted C$_n$-alkyl" refers to a radical, having a linear or branched, cyclic or acyclic structure, further having no carbon-carbon double or triple bonds, further having a total of n carbon atoms, all of which are nonaromatic, 3 or more hydrogen atoms, and no heteroatoms. For example, a heteroatom-unsubstituted C$_1$-C$_{10}$-alkyl has 1 to 10 carbon atoms. The groups —CH$_3$ (Me), —CH$_2$CH$_3$ (Et), —CH$_2$CH$_2$CH$_3$ (n-Pr), —CH(CH$_3$)$_2$ (iso-Pr), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), —CH(CH$_3$)CH$_2$CH$_3$, hexyl, cyclohexenyl, cyclohexadienyl, and

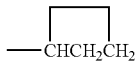

are all non-limiting examples of heteroatom-unsubstituted alkyl groups. The term "heteroatom-substituted C$_n$-alkyl" refers to a radical, having a single saturated carbon atom as the point of attachment, no carbon-carbon double or triple bonds, further having a linear or branched, cyclic or acyclic structure, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a heteroatom-substituted C$_1$-C$_{10}$-alkyl has 1 to 10 carbon atoms. The following groups are all non-limiting examples of heteroatom-substituted alkyl groups: trifluoromethyl, —CH$_2$F, —CH$_2$Cl, —CH$_2$Br, —CH$_2$OH, —CH$_2$OCH$_3$, —CH$_2$OCH$_2$CF$_3$, —CH$_2$OC(O)CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, CH$_2$CH$_2$OC(O)CH$_3$, —CH$_2$CH$_2$NHCO$_2$C(CH$_3$)$_3$, —C(=N—OH)CH(CH$_3$)$_2$ and —CH$_2$Si(CH$_3$)$_3$. In certain embodiments, "lower alkyl" groups are contemplated. As used herein, "lower alkyl" refers to an alkyl containing 1-6 carbon atoms. In certain embodiments, certain alkyl groups may be excluded.

The term "amino," alone or in combination, is used interchangeably with "amine" and may refer to any one or more of the following: a primary (e.g., —NH$_2$), secondary (e.g., alkyl-NH—), tertiary (e.g., (alkyl)$_2$-N—), or quaternary (e.g., (alkyl)$_3$-N(+)—) amine radical.

The term "aryl" includes heteroatom-unsubstituted aryl, heteroatom-substituted aryl, heteroatom-unsubstituted C$_n$-aryl, heteroatom-substituted C$_n$-aryl, heteroaryl, heterocyclic aryl groups, carbocyclic aryl groups, biaryl groups, and radicals derived from polycyclic fused hydrocarbons (PAHs). The term "heteroatom-unsubstituted C$_n$-aryl" refers to a radical, having a single carbon atom as a point of attachment, wherein the carbon atom is part of an aromatic ring structure containing only carbon atoms, further having a total of n carbon atoms, 5 or more hydrogen atoms, and no heteroatoms. For example, a heteroatom-unsubstituted C$_6$-C$_{10}$-aryl has 6 to 10 carbon atoms. Non-limiting examples of heteroatom-unsubstituted aryl groups include methylphenyl, (dimethyl)phenyl, —C$_6$H$_4$CH$_2$CH$_3$, —C$_6$H$_4$CH$_2$CH$_2$CH$_3$, —C$_6$H$_4$CH(CH$_3$)$_2$, —C$_6$H$_4$CH(CH$_2$)$_2$, —C$_6$H$_3$(CH$_3$)CH$_2$CH$_3$, —C$_6$H$_4$CH=CH$_2$, —C$_6$H$_4$CH=CHCH$_3$, —C$_6$H$_4$C≡CH, —C$_6$H$_4$C≡CCH$_3$, naphthyl, and the radical derived from biphenyl. The term "heteroatom-substituted C$_n$-aryl" refers to a radical, having either a single aromatic carbon atom or a single aromatic heteroatom as the point of attachment, further having a total of n carbon atoms, at least one hydrogen atom, and at least one heteroatom, further wherein each heteroatom is independently selected from the group consisting of N, O, F, Cl, Br, I, Si, P, and S. For example, a heteroatom-unsubstituted C$_1$-C$_{10}$-heteroaryl has 1 to 10 carbon atoms. Non-limiting examples of heteroatom-substituted aryl groups include the groups: —C$_6$H$_4$F, —C$_6$H$_4$Cl, —C$_6$H$_4$Br, —C$_6$H$_4$I, —C$_6$H$_4$OH, —C$_6$H$_4$OCH$_3$, —C$_6$H$_4$OCH$_2$CH$_3$, —C$_6$H$_4$OC(O)CH$_3$, —C$_6$H$_4$NH$_2$, —C$_6$H$_4$NHCH$_3$, —C$_6$H$_4$N(CH$_3$)$_2$, —C$_6$H$_4$CH$_2$OH, —C$_6$H$_4$CH$_2$OC(O)CH$_3$, —C$_6$H$_4$CH$_2$NH$_2$, —C$_6$H$_4$CF$_3$, —C$_6$H$_4$CN, —C$_6$H$_4$CHO, —C$_6$H$_4$CHO, —C$_6$H$_4$C(O)CH$_3$, —C$_6$H$_4$C(O)C$_6$H$_5$, —C$_6$H$_4$CO$_2$H, —C$_6$H$_4$CO$_2$CH$_3$, —C$_6$H$_4$CONH$_2$, —C$_6$H$_4$CONHCH$_3$, —C$_6$H$_4$CON(CH$_3$)$_2$, furanyl, thienyl, pyridyl, pyrrolyl, pyrimidyl, pyrazinyl, indolyl, quinolyl, and imidazoyl.

The term "aralkyl" includes heteroatom-unsubstituted aralkyl, heteroatom-substituted aralkyl, heteroatom-unsubstituted C$_n$-aralkyl, heteroatom-substituted C$_n$-aralkyl, heteroaralkyl, and heterocyclic aralkyl groups. In certain embodiments, lower aralkyls are contemplated. Aralkyls generally refer to radicals comprising the formula -alkyl-aryl. The term "lower aralkyl" refers to aralkyls of 7-12 carbon atoms (that is, 7, 8, 9, 10, 11 or 12 carbon atoms). The term "heteroatom-unsubstituted C$_n$-aralkyl" refers to a radical, having a single saturated carbon atom as the point of attachment, further having a total of n carbon atoms, wherein at least 6 of the carbon atoms form an aromatic ring structure containing only carbon atoms, 7 or more hydrogen atoms, and no heteroatoms. For example, a heteroatom-unsubstituted C$_7$-C$_{11}$-aralkyl has 7 to 11 carbon atoms. Non-limiting examples of heteroatom-unsubstituted aralkyls are: 2,3-dihydro-1H-indenyl, 1,2,3,4-tetrahydronaphthalenyl, phenylmethyl (benzyl, Bn) and phenylethyl. The term "heteroatom-substituted C$_n$-aralkyl" refers to a radical, having a single saturated carbon atom as the point of attachment, further having a total of n carbon atoms, 0, 1, or more than one hydrogen atom, and at least one heteroatom, wherein at least one of the carbon atoms is incorporated an aromatic ring structures, further wherein each heteroatom is independently selected from the group consisting of N, O, F, Cl, Br, I, Si, P. and S. For example, a heteroatom-substituted C$_2$-C$_{10}$-heteroaralkyl has 2 to 10 carbon atoms. Examples of heteroatom-substituted $C_n$-aralkyls include indolinyl, benzofuranyl and benzothiophenyl. In certain embodiments, certain aryl groups may be specifically excluded.

As used herein, a "halide" (or "halo") refers to fluoro, chloro, bromo or iodo. In certain embodiments, certain halides may be specifically excluded.

Compounds as described herein may contain one or more asymmetric centers and thus can occur as racemates and racemic mixtures, single enantiomers, diastereomeric mixtures and individual diastereomers. All possible stereoisomers of the all the compounds described herein, unless otherwise noted, are contemplated as being within the scope of the present invention. In preferred embodiments, a single diastereomer is contemplated. The chiral centers of the compounds of the present invention can have the S- or the R-configuration, as defined by the IUPAC 1974 Recommendations. The present invention is meant to comprehend all such isomeric forms of the compounds of the invention.

The claimed invention is also intended to encompass salts of any of the synthesized compounds of the present invention. The term "salt(s)" as used herein, is understood as being acidic and/or basic salts formed with inorganic and/or organic acids and bases. Zwitterions (internal or inner salts) are understood as being included within the term "salt(s)" as used herein, as are quaternary ammonium salts such as alkylammonium salts. Nontoxic, pharmaceutically acceptable salts are preferred as described below, although other salts may be useful, as for example in isolation or purification steps.

Non-limiting examples of acid addition salts include but are not limited to acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pectinate, persulfate, 3-phenylpropionate, picrate, pivalate, propionate, succinate, tartrate, thiocyanate, tosylate and undecanoate.

Non-limiting examples of basic salts include but are not limited to ammonium salts; alkali metal salts such as sodium, lithium, and potassium salts; alkaline earth metal salts such as calcium and magnesium salts; salts comprising organic bases such as amines (e.g., dicyclohexylamine, alkylamines such as t-butylamine and t-amylamine, substituted alkylamines, arylalkylamines such as benzylamine, dialkylamines, substituted dialkylamines such as N-methyl glucamine (especially N-methyl D-glucamine), trialkylamines, and substituted trialkylamines); and salts comprising amino acids such as arginine, lysine and so forth. The basic nitrogen-containing groups may be quaternized with agents such as lower alkyl halides (e.g., methyl, ethyl. propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), arylalkyl halides (e.g., benzyl and phenethyl bromides) and others known in the art.

When a chemical reaction is to be carried out selectively at one reactive site in a multifunctional compound, other reactive sites must be temporarily blocked. A "protecting group," as used herein, is defined as a group used for the purpose of this temporary blockage. During the synthesis of the compounds of the present invention, various functional groups must be protected using protecting groups (or protecting agents) at various stages of the synthesis. However, use of the phrases "protected carboxylic acid," "protected amine" or "protected hydroxy," for example, does not mean that every functional group available to be protected is protected. Functional groups necessary for the desired transformation, for example, should be unprotected.

Thus, the function of a protecting group is to protect one or more functionalities (e.g., $-NH_2$, $-SH$, $-COOH$) during subsequent reactions which would not proceed well, either because the free (in other words, unprotected) functional group would react and be functionalized in a way that is inconsistent with its need to be free for subsequent reactions, or the free functional group would interfere in the reaction. The same protecting group may be used to protect one or more of the same or different functional group(s). Also, different protecting groups can be used to protect the same type of functional group within a compound of the present invention in multiple steps. There are a number of methods well known to those skilled in the art for accomplishing such a step. For protecting agents, their reactivity, installation and use, see, e.g., Greene & Wuts, 1999.

When a protecting group is no longer needed, it is removed by methods well known to those skilled in the art. For deprotecting agents and their use, see, e.g., Greene & Wuts, 1999. Agents used to remove the protecting group are sometimes called deprotecting agents. Protecting groups must be readily removable (as is known to those skilled in the art) by methods employing deprotecting agents that are well known to those skilled in the art. It is well known that certain deprotecting agents remove some protective groups and not others, while other deprotecting agents remove several types of protecting groups from several types of functional groups. Thus, a first deprotecting agent may be used to remove one type of protecting group, followed by the use of a second deprotecting agent to remove a second type of protecting group, and so on.

In one embodiment of the present invention, the deprotecting agent is the use of gaseous $H_2$ in the presence of a palladium catalyst dispersed on carbon in order to remove a benzyl (Bn) protecting group and reveal a free carboxylic acid. Persons of ordinary skill in the art will be familiar with the proper ordering of protective group removal using deprotecting agents. See e.g., Greene & Wuts, 1999. Particular non-limiting examples of protecting groups are discussed below.

Amino protecting groups are well known to those skilled in the art. See, for example, Greene & Wuts, 1999, Chapter 7. The amino protecting group may be a carbamate. A suitable amino protecting group may be selected from the group consisting of t-butoxycarbonyl, benzyloxycarbonyl, formyl, trityl, acetyl, trichloroacetyl, dichloroacetyl, chloroacetyl, trifluoroacetyl, difluoroacetyl, fluoroacetyl, benzyl chloroformate, 4-phenylbenzyloxycarbonyl, 2-methylbenzyloxycarbonyl, 4-ethoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluoyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluoylsulfonyl)ethoxycarbonyl, 2-(methylsulfonyl)ethoxycarbonyl, 2-(triphenylphosphino) ethoxycarbonyl, fluorenylmethoxycarbonyl, 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxyl)benzyloxycarbonyl, isobornyloxycarbonyl, 1-piperidyloxycarbonyl and 9-fluorenylmethylcarbonyl, for example. In certain embodiments of the present invention, the amine protecting group is t-butoxycarbonyl (Boc), benzyloxycarbonyl (CBz), paramethoxybenzyl (PMB), or 9-fluorenylmethylcarbonyl (Fmoc).

Thiol protecting groups are well known to those skilled in the art. See, for example, Greene & Wuts, 1999, Chapter 6. A suitable thiol protecting group may be selected from the group consisting of acetamidomethyl, benzamidomethyl, 1-ethoxyethyl, benzoyl, triphenylmethyl, t-butyl, benzyl, adamantyl, cyanoethyl, acetyl, and trifluoroacetyl, for example.

Alcohol protecting groups are well known to those skilled in the art. See, for example, Greene & Wuts, 1999, Chapter 2. A suitable alcohol protecting group may be selected from the group consisting of methoxymethyl, paramethoxybenzyl, (phenyldimethylsilyl)methoxymethyl, triethylsilyl, benzyloxymethyl, t-butoxymethyl, and tetrahydropyranyl, for example. In certain embodiments of the present invention, the an alcohol protecting group is benzyl (Bn), paramethoxybenzyl (PMB), or triethylsilyl (TES).

Carboxylic acid protecting groups are well known to those skilled in the art. See, for example, Greene & Wuts, 1999, Chapter 5. A suitable carboxylic acid protecting group may be selected from the group consisting of dimethylacetal, methoxymethylester, phenylacetoxymethyl ester and tetrahydropyranyl ester, for example. In certain embodiments of the present invention, the carboxylic acid protecting group is benzyl (Bn). As used herein, a "protected carboxylic acid" refers to a carboxylic acid group protected by a carboxylic acid protecting group.

The compounds, agents, and active ingredients (e.g., solvents, catalysts, bases used in reactions, and other compounds, agents, and active ingredients described herein) that are described in the claims and specification can be obtained by any means known to a person of ordinary skill in the art. In a non-limiting embodiment, for example, the compounds, agents, and active ingredients can be isolated by obtaining the source of such compounds, agents, and active ingredients. In many instances, the compounds, agents, and active ingredients are commercially available (e.g., Sigma-Aldrich, Milwaukee, Wis.).

Modifications or derivatives of the compounds, agents, and active ingredients disclosed throughout this specification are contemplated as being useful with the methods and compositions of the present invention. Derivatives may be prepared and the properties of such derivatives may be assayed for their desired properties by any method known to those of skill in the art.

In certain aspects, "derivative" refers to a chemically modified compound that still retains the desired effects of the compound prior to the chemical modification. Such derivatives may have the addition, removal, or substitution of one or more chemical moieties on the parent molecule. Non-limiting examples of the types modifications that can be made to the compounds and structures disclosed herein include the addition or removal of lower alkanes such as methyl, ethyl, propyl, or substituted lower alkanes such as hydroxymethyl or aminomethyl groups; carboxyl groups and carbonyl groups; hydroxyls; nitro, amino, amide, and azo groups; sulfate, sulfonate, sulfono, sulfhydryl, sulfonyl, sulfoxido, phosphate, phosphono, phosphoryl groups, and halide substituents. Additional modifications can include an addition or a deletion of one or more atoms of the atomic framework, for example, substitution of an ethyl by a propyl; substitution of a phenyl by a larger or smaller aromatic group. Alternatively, in a cyclic or bicyclic structure, hetero atoms such as N, S, or O can be substituted into the structure instead of a carbon atom.

2. Pharmaceutical Formulations and Administration Thereof

A. Pharmaceutical Formulations and Routes for Administration to Subjects

Pharmaceutical compositions of the present invention comprise an effective amount of one or more candidate substance or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one candidate substance or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The candidate substance may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, subcutaneously, subconjunctival, intravesicularlly, mucosally, intrapericardially, intraumbilically, intraocularally, orally, locally, via inhalation (e.g., aerosol inhalation), via injection, via infusion, via continuous infusion, via localized perfusion bathing target cells directly, via a catheter, via a lavage, in cremes, in lipid compositions (e.g., liposomes), or by other method or any combination of the foregoing as would be known to one of ordinary skill in the art (see, for example, Remington's Pharmaceutical Sciences, 1990).

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of a compound of the present invention. In other embodiments, the compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal, or combinations thereof.

The candidate substance may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine, or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. It may be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in certain embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the candidate substance is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. In certain embodiments, carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar, or both.

Additional formulations which are suitable for other modes of administration include suppositories. Suppositories are solid dosage forms of various weights and shapes, usually medicated, for insertion into the rectum, vagina, or urethra. After insertion, suppositories soften, melt or dissolve in the cavity fluids. In general, for suppositories, traditional carriers may include, for example, polyalkylene glycols, triglycerides, or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, certain methods of preparation may include vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin, or combinations thereof.

B. Combination Therapy

In order to increase the effectiveness of a compound of the present invention, the compound may be combined with traditional drugs. It is contemplated that this type of combination therapy may be used in vitro or in vivo. In a non-limiting example, an anti-cancer agent may be used in combination with a compound. An anti-viral or antibiotic agent may be used in combination with a compound, for example.

More generally, agents of the present invention may be provided in a combined amount with an effective amount of an anti-cancer agent. This process may involve contacting the cell(s) with the agents at the same time or within a period of time wherein separate administration of the substances produces a desired therapeutic benefit. This may be achieved by contacting the cell, tissue or organism with a single composition or pharmacological formulation that includes two or more agents, or by contacting the cell with two or more distinct compositions or formulations, wherein one composition includes one agent and the other includes another.

The compounds of the present invention may precede, be co-current with and/or follow the other agents by intervals ranging from minutes to weeks. In embodiments where the agents are applied separately to a cell, tissue or organism, one would generally ensure that a significant period of time did not expire between the time of each delivery, such that the agents would still be able to exert an advantageously combined effect on the cell, tissue or organism. For example, in such instances, it is contemplated that one may contact the cell, tissue or organism with two, three, four or more modalities substantially simultaneously (i.e., within less than about a minute) as the candidate substance. In other aspects, one or more agents may be administered within of from substantially simultaneously, about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 1, about 2, about 3, about 4, about 5, about 6, about 7 or about 8 weeks or more, and any range derivable therein, prior to and/or after administering the candidate substance.

Various combination regimens of the agents may be employed. Non-limiting examples of such combinations are shown below, wherein a compound is "A" and a second agent, such as an anti-cancer agent, is "B":

A/B/A B/A/B B/B/A A/A/B A/B/B B/A/A A/B/B/B

B/A/B/B B/B/B/A B/B/A/B A/A/B/B A/B/A/B A/B/B/A

B/B/A/A B/A/B/A B/A/A/B A/A/A/B B/A/A/A A/B/A/A

A/A/B/A

An "anti-cancer" agent is capable of negatively affecting cancer in a subject, for example, by killing one or more cancer cells, inducing apoptosis in one or more cancer cells, reducing the growth rate of one or more cancer cells, reducing the incidence or number of metastases, reducing tumor size, inhibiting tumor growth, reducing the blood supply to a tumor or one or more cancer cells, promoting an immune response against one or more cancer cells or a tumor, preventing or inhibiting the progression of a cancer, or increasing the lifespan of a subject with a cancer. Anti-cancer agents are well-known in the art and include, for example, chemotherapy agents (chemotherapy), radiotherapy agents (radiotherapy), a surgical procedure, immune therapy agents (immunotherapy), genetic therapy agents (gene therapy), reoviral therapy, hormonal therapy, other biological agents (biotherapy), and/or alternative therapies.

2. Examples

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

General

Figure 2:
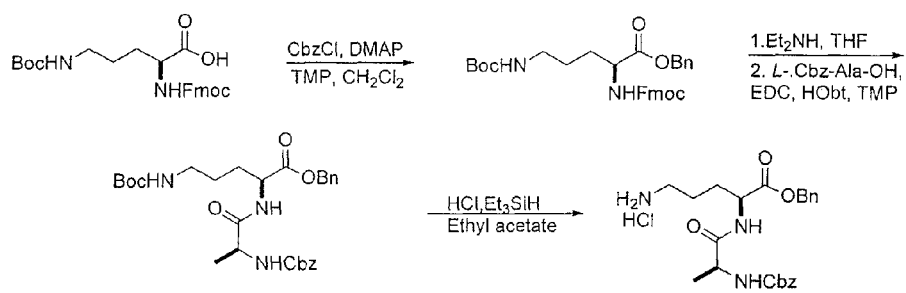
FIG. 2. General synthetic method for belactosin C and derivatives: Synthesis of dipeptide and beta-lactone separately, followed by coupling.
Figure 2:
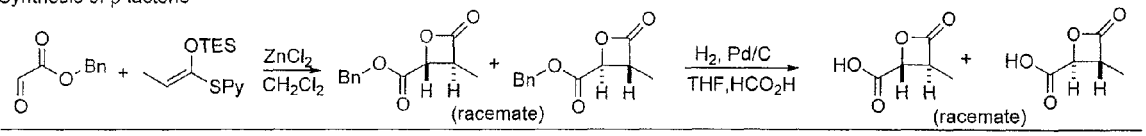
Figure 2:
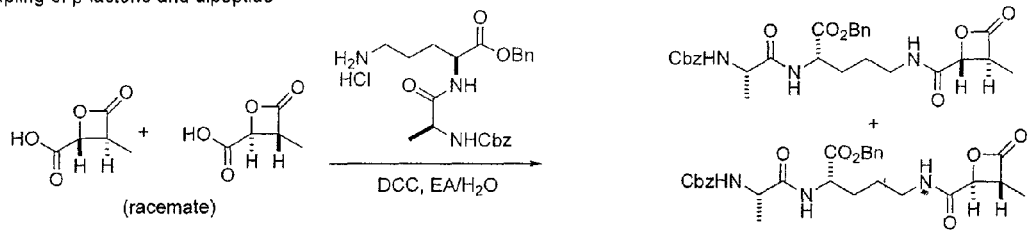

FIGS. 1 and 2 represent, in certain embodiments, general synthetic methods for accessing compounds of the present invention.

Protected ornithine and alanine were purchased from Acros and used as received. Other reagents were purchased from Aldrich (Milwaukee, Wis.) and used as received.

Example 1

Synthesis of a Vinyl Amide

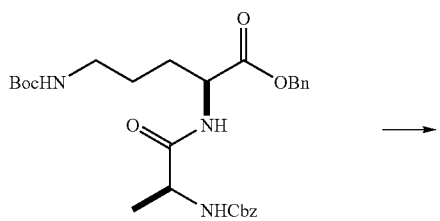

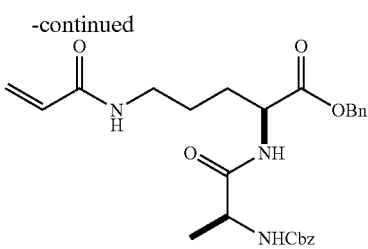

To a stirred solution of the dipeptide of Example 2 (28.00 g, 53.07 mmol) and Et$_3$SiH (25.71 g, 159.21 mmol) in Ethyl acetate (300 mL) was added HCl (10.47 mL, 106.14 mmol). The reaction mixture was stirred for 16 h at room temperature, and then the solvent was evaporated. To the resulting residue was poured hexane (500 mL), and stirred to give a white solid. The resulting free amine solid was filtered and can be used for next step without further purification.

To a stirred solution of free amine (25.00 g, 53.89 mmol) and TMP (22.74 g, 134.7 mmol) in CH$_2$Cl$_2$ (300 mL) was added acryloyl chloride (5.25 g, 64.7 mmol) at 0° C. The reaction mixture was stirred for 4 h at 0° C. and then quenched by slow additional 1N HCl (100 mL) and neutralized by washing with saturated NaHCO$_3$ solution (100 mL×2). The organic layer was separated and evaporated to give a crude solid. The crude compound was triturated by pentane to give the acrylamide peptide (24.0 g, 92.5%). IR (thin film) 2937, 1796, 1728, 1665, 1536, 1403 cm$^{-1}$; $^1$H NMR (500 MHz, CDCl$_3$) δ 7.32-7.43 (m, 10H), 6.99 (s, 1H), 6.26 (d, J=4.2 Hz, 1H), 6.04 (dd, J=9.9, 16.6 Hz, 2H), 5.12 (m, 2H), 4.60 (m, 1H), 4.28 (m, 1H), 3.27 (m, 2H), 1.82-1.96 (m, 1H), 1.61-1.73 (m, 1H), 1.42-1.58 (m, 2H), 1.41 (d, J=6.9 Hz, 3H); $^{13}$C NMR (125 MHz, CDCl$_3$) δ 172.6, 171.7, 165.8, 136.1, 135.1, 130.8, 128.7, 128.6, 128.5, 128.4, 128.2, 128.0, 126.5, 67.4, 67.1, 52.1, 50.6, 38.7, 29.4, 25.4, 18.5; LRMS (ESI) Calcd. for C$_{26}$H$_{32}$N$_3$O$_6$ [M+H]$^+$: 482. Found: 482.

Example 2

Synthesis of an Oxoaldehyde

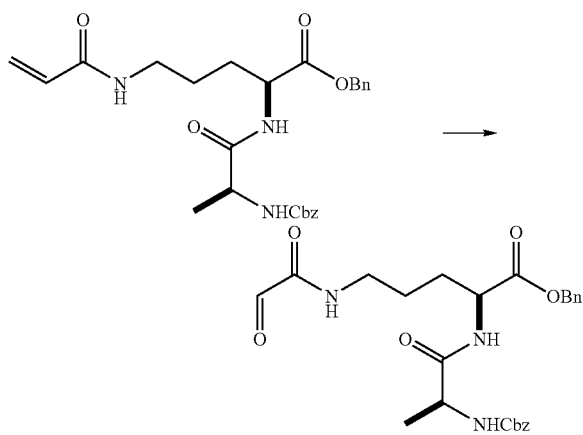

To a stirred solution of acrylamide (5.00 g, 10.4 mmol) in CH$_2$Cl$_2$ (200 mL) and MeOH (1 mL) was bubbled ozone at 78° C. until the blue color persisted, and the remaining ozone was removed bubbling nitrogen through the solution. Dimethyl sulfide (3.05 mL, 41.6 mmol) was added and the mixture was left to attain 25° C. for 12 h. The solvent was evaporated under reduced vacuum and the resulting oil was purified by flash chromatography on SiO$_2$ (CH$_2$Cl$_2$/acetone=1/1) to afford a mixture of hydrate and glyoxylate (3.02 g, 60%) as a white solid. The resulting mixture of hydrate and glyoxylate was dissolved into CH$_2$Cl$_2$ with 4 Å Molecular sieve and stirred for 24 h at room temperature to give glyoxylate. The resulting glyoxylate was used directly in the next step without further purification.

Example 3

Synthesis of a Ketene Acetal

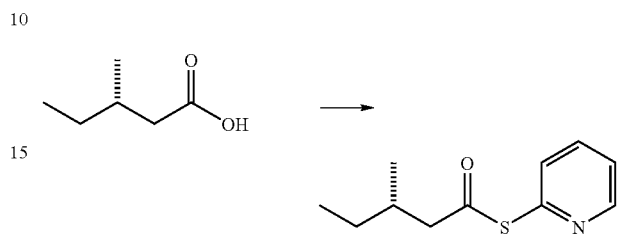

To a stirred solution of acid (1.24 g, 10.7 mmol) in CH$_2$Cl$_2$ (30 mL) was added oxalyl chloride (1.38 mL, 16.0 mmol) at 25° C. The reaction mixture was stirred for 2 h at 25° C. The solvent was evaporated under reduced pressure. To a stirred solution of the oil residue was added 2-thiopyridine (1.42 g, 12.8 mmol) in CH$_2$Cl$_2$ (30 mL) followed by Et$_3$N (2.98 mL, 21.3 mmol) at 0° C. The reaction mixture was stirred for 2 h at 25° C. and then quenched with 1N HCl (30 mL) and neutralized by washing with saturated NaHCO$_3$ solution (30 mL×2). The organic layers were combined and evaporated, then resulting yellow oil was purified by flash chromatography on SiO$_2$ (20% EtOAc/Hexane) to afford acid ester (2.19 g, 98%) as a pure liquid: [α]$_D^{20}$+8.2 (c=0.027, CHCl$_3$). IR (thin film) 2953, 1702, 1440, 1418 cm$^{-1}$; $^1$H NMR (300 MHz, CDCl$_3$) δ 8.64 (m, 1H), 7.75 (m, 1H), 7.64 (m, 1H), 7.31 (m, 1H), 2.73 (dd, J=6.3, 14.7 Hz, 1H), 2.54 (dd, J=7.8, 14.7 Hz, 1H), 1.96-2.10 (m, 1H), 1.42-1.49 (m, 1H), 1.29-1.35 (m, 1H), 0.97 (d, J=6.3 Hz, 3H), 0.91 (t, J=7.8 Hz, 3H); $^{13}$C NMR (125 MHz, CDCl$_3$) δ 196.4, 151.9, 150.5, 137.4, 130.4, 123.7, 51.3, 32.8, 29.5, 19.4, 11.5; LRMS (ESI) Calcd. for C$_{11}$H$_{16}$NOS [M+H]$^+$: 210. Found: 210.

Example 4

(S,E)-2-(3-methyl-1-(triethylsilyloxy)pent-1-enylthio)pyridine

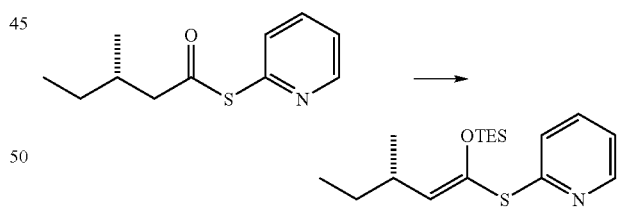

To a stirred solution of thioester (8.00 g, 35.8 mmol), DMF (3.14 g, 43.0 mmol) and Et$_3$N (6.04 g, 43.0 mmol) in CH$_2$Cl$_2$ (240 mL) was added LiHMDS (1.0M, 82.6 mL, 82.6 mmol) at 78° C. The reaction mixture was stirred for 30 min at 78° C. and TESCl (12.02 mL, 71.6 mmol) was added dropwise to the reaction mixture at ~78° C. The reaction mixture was stirred for 2 h at this temperature and then quenched with pH 7 buffer solution (40 mL×2). The organic layer was separated, dried over Na$_2$SO$_4$ and evaporated. The resulting yellowish oil was purified by flash chromatography on SiO$_2$ (10% EtOAc/Hexane) to afford ketene acetal (11.1 g, 96.2%) as a yellow oil: [α]$_D^{20}$+1.8 (c=0.034, CHCl$_3$). IR (thin film) cm$^{-1}$; 2950, 2873, 1624, 1568 cm$^{-1}$; $^1$H NMR (300 MHz, CDCl$_3$) δ 8.40 (m, 1H), 7.53 (m, 1H), 7.32 (m, 1H), 6.97 (m, 1H), 5.18 (d, J=9.6, 1H), 2.58 (m, 1H), 1.33-1.40 (m, 2H), 1.00 (d, J=6.6 Hz, 3H), 0.93 (t, J=7.5 Hz, 3H), 0.84-0.89 (m, 9H), 0.60-0.68

(m, 6H); $^{13}$C NMR (125 MHz, CDCl$_3$) δ 160.9, 149.6, 138.7, 136.8, 130.5, 122.3, 121.5, 119.9, 119.8, 33.5, 30.1, 20.4, 12.3, 6.8; LRMS (ESI) Calcd. for C$_{11}$H$_{16}$NOS[M+H]$^+$: 324. Found: 324.

General Procedure for the Tandem Mukaiyama Aldol Lactonization (TMAL) Reaction Under Normal Conditions (GP1)

Anhydrous ZnCl$_2$ (1.2-2.0 equiv) was freshly fused at ~0.5 mm Hg and after cooling to ambient temperature, CH$_2$Cl$_2$ (appropriate volume to make final concentration of aldehyde in CH$_2$Cl$_2$ ~0.2 M) was added. The aldehyde (1.0 equiv) was then added neat or as a CH$_2$Cl$_2$ solution at room temperature followed by thiopyridyllketene acetal (1.1-1.2 equiv) neat. The suspension was stirred for the appropriate time, and then quenched by pH 7 buffer, filtered. The organic layer was dried over Na$_2$SO$_4$, filtered, and concentrated in vacuo to afford the crude product which was purified by flash chromatography

Example 5

Synthesis of a Beta-Lactone

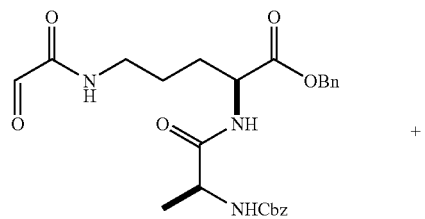

+

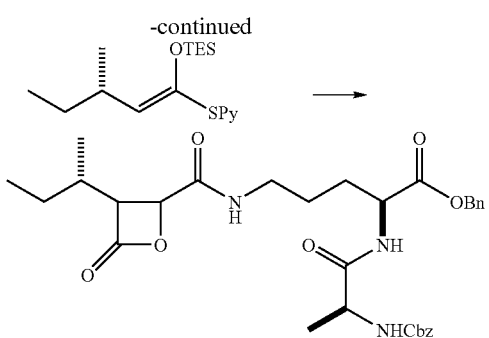

To a stirred solution of ketene acetal (96.74 mg, 0.30 mmol) and fused ZnCl$_2$ (81.57 mg, 0.60 mmol) in CH$_2$Cl$_2$ (5 mL), was added via canula activated Molecular sieve 4 Å (100 mg) and oxoaldehyde (100 mg, 0.20 mmol) in CH$_2$Cl$_2$ (5 mL). The solution was stirred for 36 h at room temperature, and then quenched by pH 7 buffer (5 mL), filtered. The organic layer was separated and evaporated under reduced pressure and the residue, an oily solid, was purified by flash chromatography on SiO$_2$ (100% ethyl acetate) to afford beta-lactone (30 mg, 15%) as a colorless oil.

Example 6

Diastereoselective TMAL via a Chiral Auxiliary Approach

Synthesis of Belactosin C and all Diastereomers of the Beta-Lactone Moiety

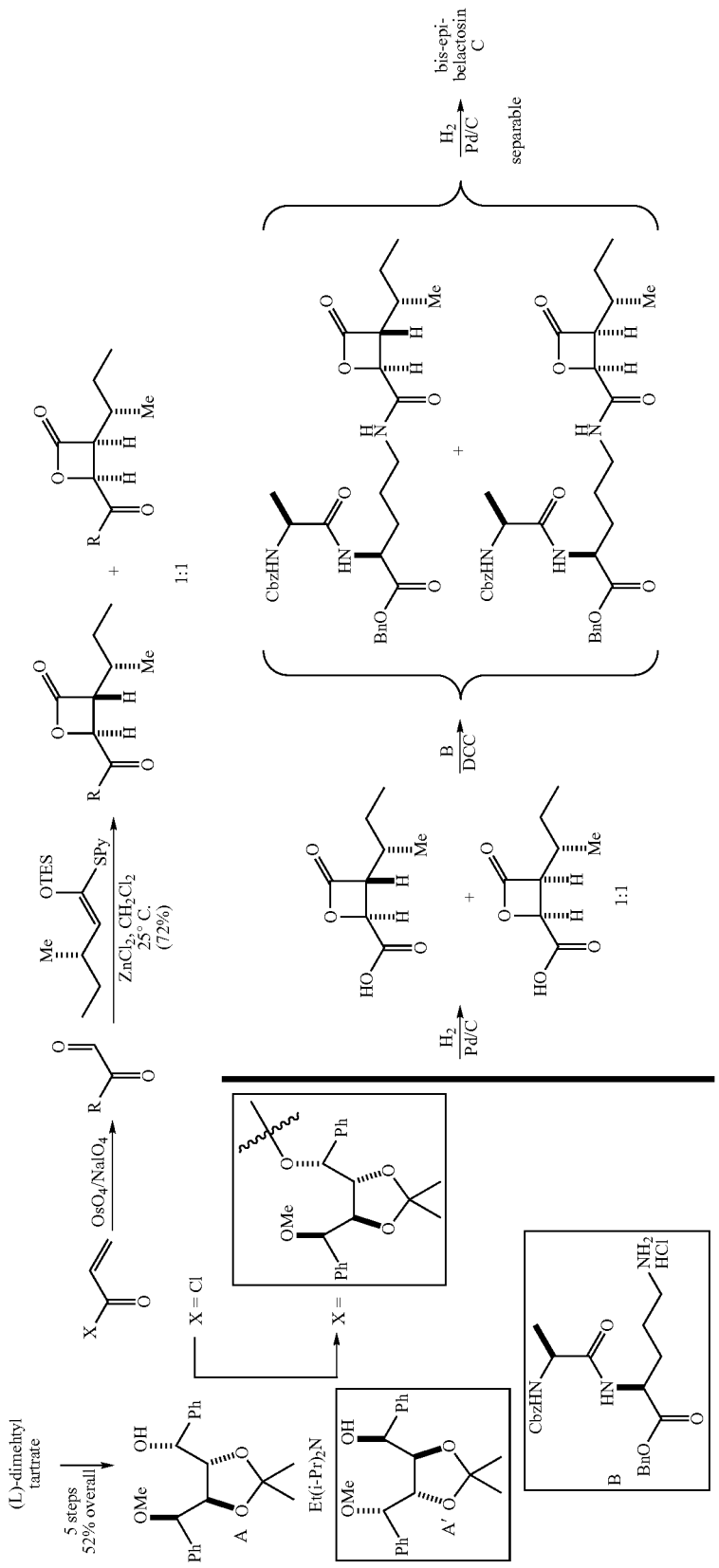

Previously, the present inventors obtained poor diastereoselectivity in the TMAL process toward belactosin derivatives. Thus, a new chiral auxiliary A was developed from (−)-L-dimethyl tartrate (5 steps, 52% overall yield). The novel auxiliary A was prepared based on procedures for related auxiliaries. Prasad and Chandrakumar, 2005; PCT International Pub. No. WO 04/007506. The auxiliary A is converted to a glyoxaldehyde by reaction with acryolyl chloride followed by oxidative cleavage of the alkene. TMAL reaction with this chiral glyoxaldehyde delivers an ~1:1 mixture of a trans and a cis-diastereomer (72% combined yield). Removal of the chiral auxiliary by hydrogenolysis gave the beta-lactone acid, which was coupled with protected dipeptide to generate a 1:1 mixture of diastereomeric protected belactosin derivatives. The cis/trans diastereomers were separable and this particular auxiliary ((S)-((4R,5R)-5-((S)-methoxy(phenyl)methyl)-2,2-dimethyl-1,3-dioxolan-4-yl) (phenyl)methanol) gave the diastereomeric beta-lactone relative to the natural product that would deliver bis-epi-belactosin C. Preparations of the enantiomeric auxiliary A' should provide the desired belactosin C stereochemistry. Importantly, this methodology allows for preparation and separation of all diastereomers of the beta-lactone moiety found in the belatosins.

Example 7

Mono Alcohol

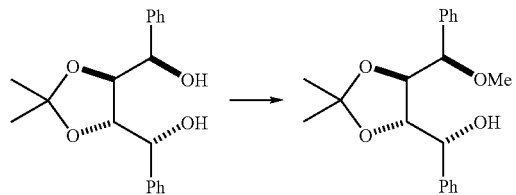

To a stirred solution of diol (4.0 g, 12.7 mmol) and $K_2CO_3$ (5.3 g, 38.2 mmol) in acetone (100 mL) was added MeI (7.9 g, 127.2 mmol) at 25° C. The reaction was refluxed for 24 h and then cooled to 25° C. The reaction mixture was filtered and evaporated to give a crude oily solid (3.8 g, 90%). The crude compound was purified by flash chromatography: $[\alpha]_D^{20}$ 11.9 (c=0.16, $CHCl_3$); IR (thin film) 3446, 2984, 2937, 1456 $cm^{-1}$; [1]; $^1H$ NMR (500 MHz, $CDCl_3$) δ 7.11-7.40 (m, 10H), 4.26 (dd, J=6.5, 7.5 Hz, 1H), 4.04 (dd, J=4.0, 7.5 Hz, 1H), 3.94 (d, J=6.5 Hz, 1H), 3.87 (dd, J=3.5, 7.5 Hz, 1H), 3.24 (s, 3H), 3.01 (d, J=7.5 Hz, 1H), 1.51 (s, 3H), 1.45 (s, 3H); $^{13}C$ NMR (125 MHz, $CDCl_3$) δ 141.3, 137.6, 128.9, 128.9, 128.6, 128.1, 128.0, 126.7, 110.4, 85.0, 81.4, 80.7, 72.9, 57.1, 27.7, 27.6; LRMS (ESI) Calcd. for $C_{11}H_{15}NOSLi[M+Li]^+$: 335. Found: 335.

Example 8

Vinyl Ester

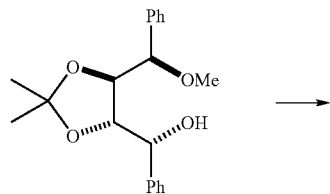

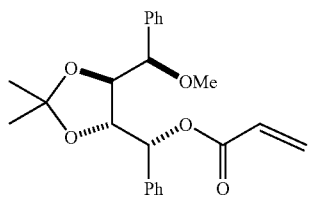

To a stirred solution of alcohol (16.00 g, 28.7 mmol) and Hunig's base (6.02 g, 34.5 mmol) in $CH_2Cl_2$ (300 mL) was added acryloyl chloride (2.79 g, 34.5 mmol) at 0° C. The reaction mixture was stirred for 12 h at 25° C. and then quenched with 1N HCl (100 mL), neutralized by washing with saturated $NaHCO_3$ solution (100 mL×2). The organic layer was separated and evaporated to give an oily solid, which was purified by flash chromatography give a white solid (10.1 g, 83.3%): $[\alpha]_D^{20}$ 15.4 (c=0.25, $CHCl_3$); IR (thin film) 2978, 2925, 1727 $cm^{-1}$; $^1H$ NMR (300 MHz, $CDCl_3$) δ 7.11-7.41 (m, 10H), 6.46 (dd, J=1.5, 17.4 Hz, 1H), 6.17 (dd, J=10.5, 20.1 Hz, 1H), 5.87 (dd, J=1.5, 10.5 Hz, 1H), 5.03 (d, J=3.9 Hz, 1H), 4.16 (m, 2H), 3.86 (d, J=6.0 Hz, 1H), 3.22 (s, 3H), 1.52 (s, 3H), 1.49 (s, 3H); $^{13}C$ NMR (125 MHz, $CDCl_3$) δ 165.2, 137.6, 137.4, 131.5, 129.0, 128.9, 128.6, 128.5, 128.0, 127.4, 110.9, 84.9, 80.7, 80.0, 75.1, 57.0, 27.9, 27.5; LRMS (ESI) Calcd. for $C_{11}H_{15}NOSLi[M+Li]^+$: 389. Found: 389.

Example 9

Glyoxylate

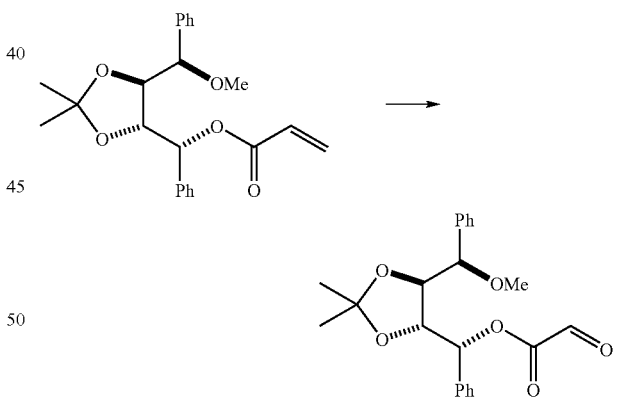

To a stirred solution of acrylate (2.70 g, 7.06 mmol) in $CH_2Cl_2$ (60 mL)/$H_2O$(40 mL) was added $OsO_4$ (0.03 g, 0.35 mmol) and $NaIO_4$ (8.39 g, 28.2 mmol) at 0° C. The reaction mixture was stirred for 2 h at 0° C., then water was added and the mixture was extracted with $Et_2O$. The organic layer was separated and evaporated to give an oily solid, which was purified by flash chromatography to afford a mixture of hydrate and desired glyoxaldehyde (2.67 g, 98%). The resulting mixture of hydrate and glyoxaldehyde was dissolved into $CH_2Cl_2$ with 4 Å Molecular sieve and stirred for 24 h at room temperature to give glyoxylate. The resulting glyoxylate was used directly in the next step without further purification.

Example 10

Beta-Lactone

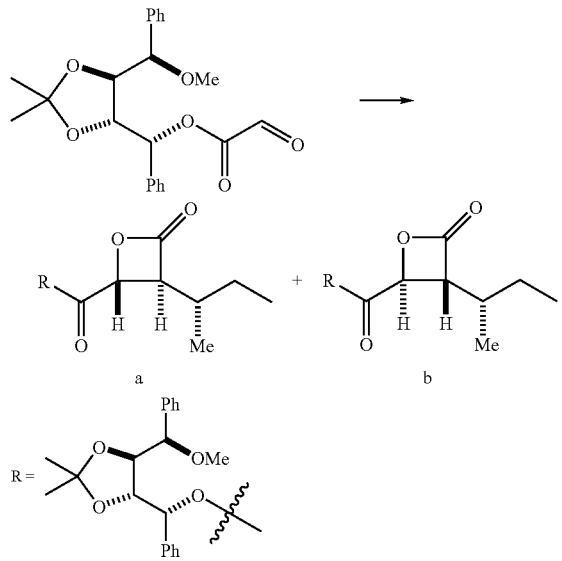

The beta-lactone a (5.0 mg, 5%) was prepared from glyoxylate (79.7 mg, 0.20 mmol) according to GP 1 as a white solid.: $[\alpha]_D^{20}$ 71.2 (c=0.38, EtOAc); IR (thin film) 2917, 1843, 1733 cm$^{-1}$; $^1$H NMR (500 MHz, CDCl$_3$) δ 7.14-7.37 (m, 10H), 5.20 (d, J=5.5 Hz, 1H), 4.67 (d, J=4.5 Hz, 1H), 4.19 (dd, J=6.0, 7.5 Hz, 1H), 4.03 (dd, J=6.0, 6.0 Hz, 1H), 3.69 (d, 5.5 Hz, 1H), 3.65 (dd, J=4.5, 7.5 Hz, 1H), 3.16 (s, 3H), 2.00 (m, 1H), 1.62 (m, 1H), 1.48 (s, 3H), 1.45 (s, 3H), 1.33 (m, 1H), 1.07 (d, 7.0 Hz, 3H), 0.92 (t, 7.0 Hz, 3H); $^{13}$C NMR (125 MHz, CDCl$_3$) δ 169.0, 167.6, 137.5, 136.1, 129.2, 128.9, 128.5, 127.8, 127.7, 111.0, 84.2, 80.8, 79.4, 69.3, 62.9, 57.1, 33.8, 27.8, 27.5, 27.0, 16.6, 11.2; LRMS (ESI) Calcd. for C$_{11}$H$_{15}$NOSNa[M+Na]$^+$: 505. Found: 505.

The beta-lactone b (30.0 mg, 30%) was prepared from glyoxylate 14 (79.7 mg, 0.20 mmol) according to GP 1 as a white solid.: $[\alpha]_D^{20}$ 51.6 (c=0.56, EtOAc). IR (thin film) 2917, 1843, 1733 cm$^{-1}$; $^1$H NMR (500 MHz, CDCl$_3$) δ 7.16-7.39 (m, 10H), 5.17 (d, J=5.5 Hz, 1H), 4.68 (d, J=4.5 Hz, 1H), 4.19 (dd, J=5.0, 6.5 Hz, 1H), 4.06 (dd, J=6.0, 6.0 Hz, 1H), 3.75 (d, 6.0 Hz, 1H), 3.49 (dd, J=4.5, 9.0 Hz, 1H), 3.16 (s, 3H), 1.98 (m, 1H), 1.59 (m, 1H), 1.48 (s, 3H), 1.47 (s, 3H), 1.22 (m, 1H), 1.10 (d, 7.0 Hz, 3H), 0.94 (t, 7.0 Hz, 3H); $^{13}$C NMR (125 MHz, CDCl$_3$) δ 168.7, 167.5, 137.4, 136.1, 129.2, 129.0, 128.9, 128.9, 127.9, 127.6, 111.1, 84.5, 80.9, 79.5, 77.1, 70.3, 63.4, 57.1, 34.4, 27.9, 27.6, 27.5, 16.4, 11.1; LRMS (ESI) Calcd. for C$_{11}$H$_{15}$NOSNa[M+Na]$^+$: 505. Found: 505.

Example 11

Beta-Lactone Acid

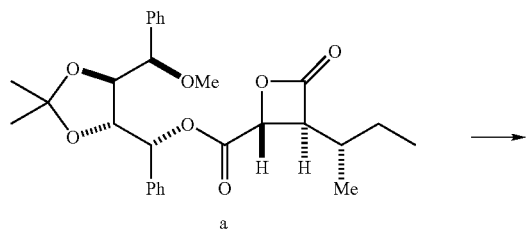

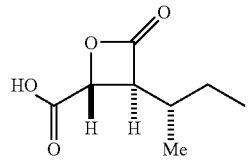

To a solution of beta-lactone a (80.3 mg, 0.16 mmol) in THF (3.0 mL) was added Pd/C and HCO$_2$H (2.0 mL). The mixture was stirred under at atmosphere of H$_2$ (rubber balloon) for 17 h. The catalyst was filtered off through a pad of cotton wool and the solvent was removed under reduced pressure to give an oily liquid, which was purified by flash chromatography give beta-lactone acid (21.2 mg, 77.0% yield) was obtained as an oily liquid: $[\alpha]_D^{20}$ 3.1 (c=0.59, CHCl$_3$). All other data matched that previously reported (Kumaraswamy, 2006).

Example 12

N-CBZ-O-Bn Protected Belactosin C

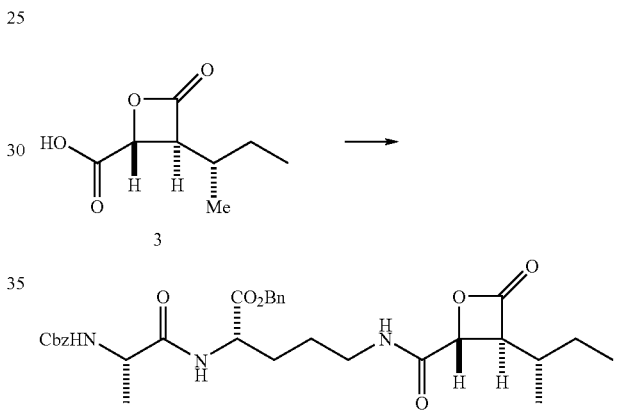

Coupling of dipeptide (34.8 mg, 0.075 mmol) and beta-lactone acid 3 (15.2 mg, 0.088 mmol) was accomplished according to the published procedure (Kumaraswamy, 2006) employing DCC (24.8 mg, 0.12 mmol) and HOBT (16.2 mg, 0.12 mmol) in 1.0 mL EtOAc/H$_2$O (1:1 ratio) to provide amide 15 (23.4 mg, 53.7%) as a colorless solid: $[\alpha]_D^{20}$+3.2 (c=0.72, CHCl$_3$). All other data matched that previously reported (Kumaraswamy, 2006).

Example 13

Biological Activity of Belactosin Derivatives

Fluorogenic Assay for Detection of 20S Proteasome

Figure 3:
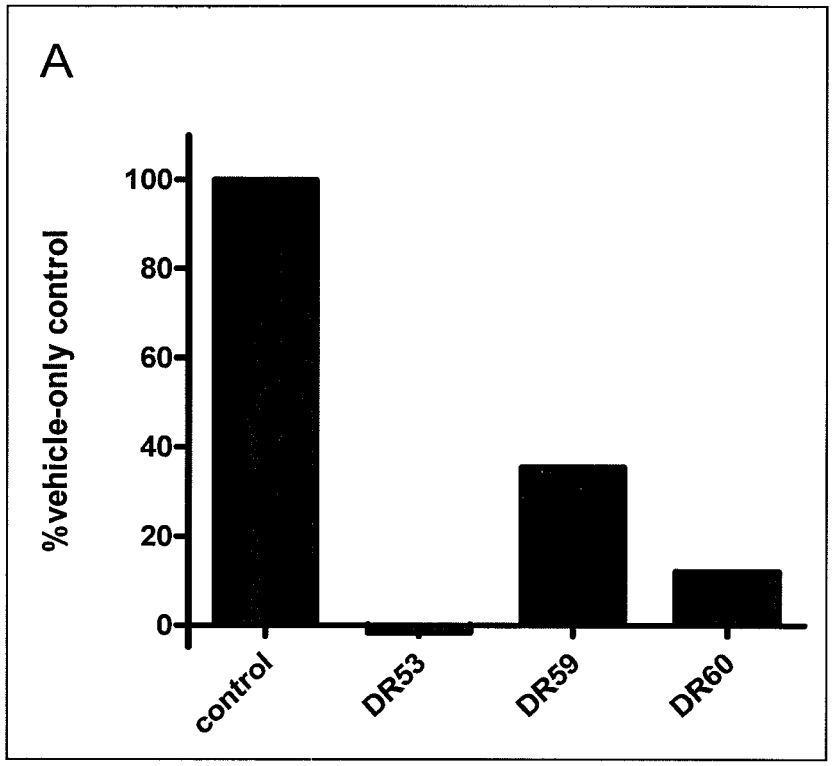
FIG. 3. Proteasome 20S inhibition assays. Known and novel belactosin derivatives inhibit the turnover of a fluorogenic substrate by the 20S proteasome. The 20S proteasome (5 nM) was incubated with (A) 1.25 µM or (B) 50 µM test compound and 100 mM suc-LLVY-AMC substrate. Fluorescence measurements were taken every ten minutes at $^{380}\!/_{460}$ nm. Results shown are the average of (A) triplicate or (B) duplicate data points.
Figure 3:
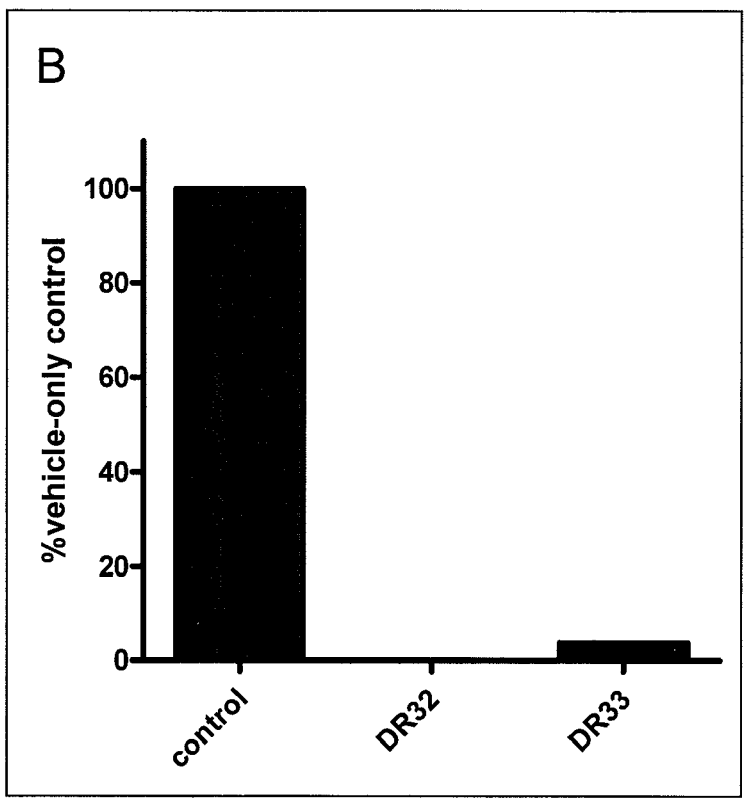

The fluorogenic peptide substrate Suc-LLVY-AMC was purchased from Biomol International, Inc. (Plymouth Meeting, Pa.). The reaction mixture consisted of approximately 5 nM 20S proteasome in buffer (50 mM Tris-HCl, pH 7.5, 1 mM DTT, 1% v/v DMSO, 5 mM MgCl$_2$, and 0.02% SDS) and 1 µL test compounds dissolved in DMSO at final concentrations of 0.4-50 µM along with 100 µM Suc-LLVY-AMC. The resulting fluorescence from liberated AMC was measured every ten minutes at $^{380}$/$_{460}$ nm for 2-3 hours. Suc-LLVY-Amc incubated without proteasome served as a background control. Results are the average of triplicate time points. The results are shown below and in FIG. 3:

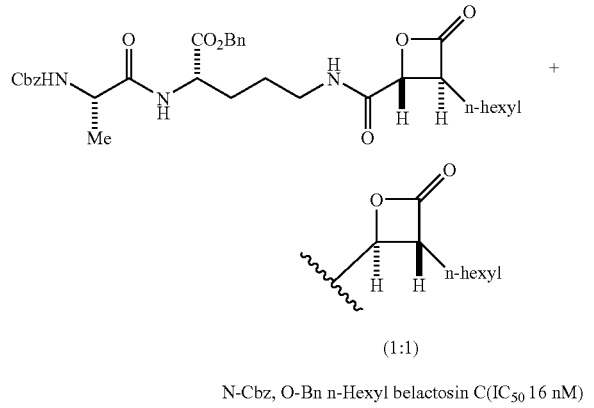

(1:1)

N-Cbz, O-Bn n-Hexyl belactosin C (IC$_{50}$ 16 nM)

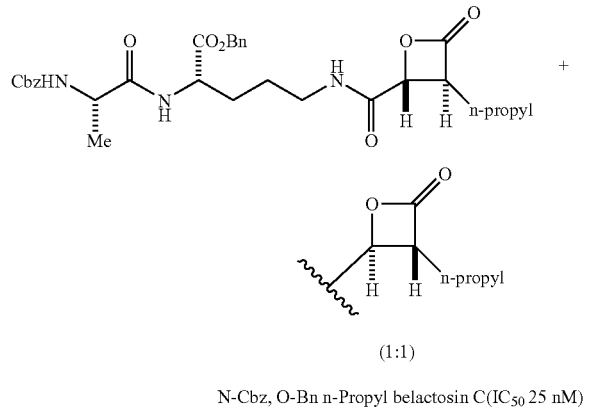

(1:1)

N-Cbz, O-Bn n-Propyl belactosin C (IC$_{50}$ 25 nM)

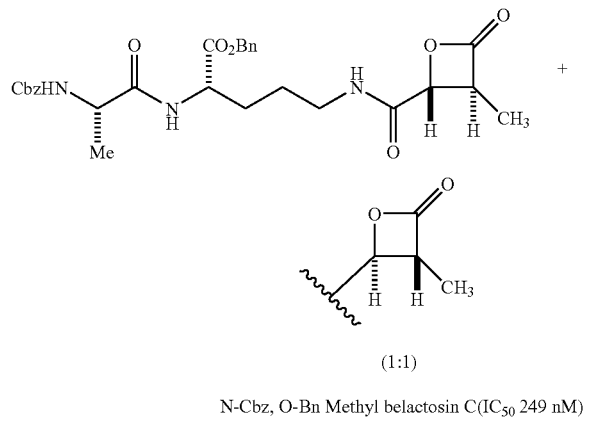

(1:1)

N-Cbz, O-Bn Methyl belactosin C (IC$_{50}$ 249 nM)

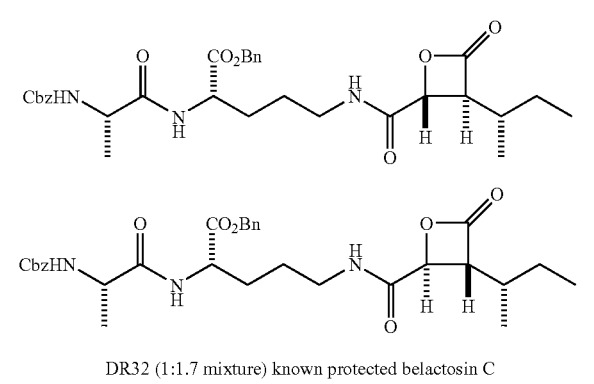

DR32 (1:1.7 mixture) known protected belactosin C

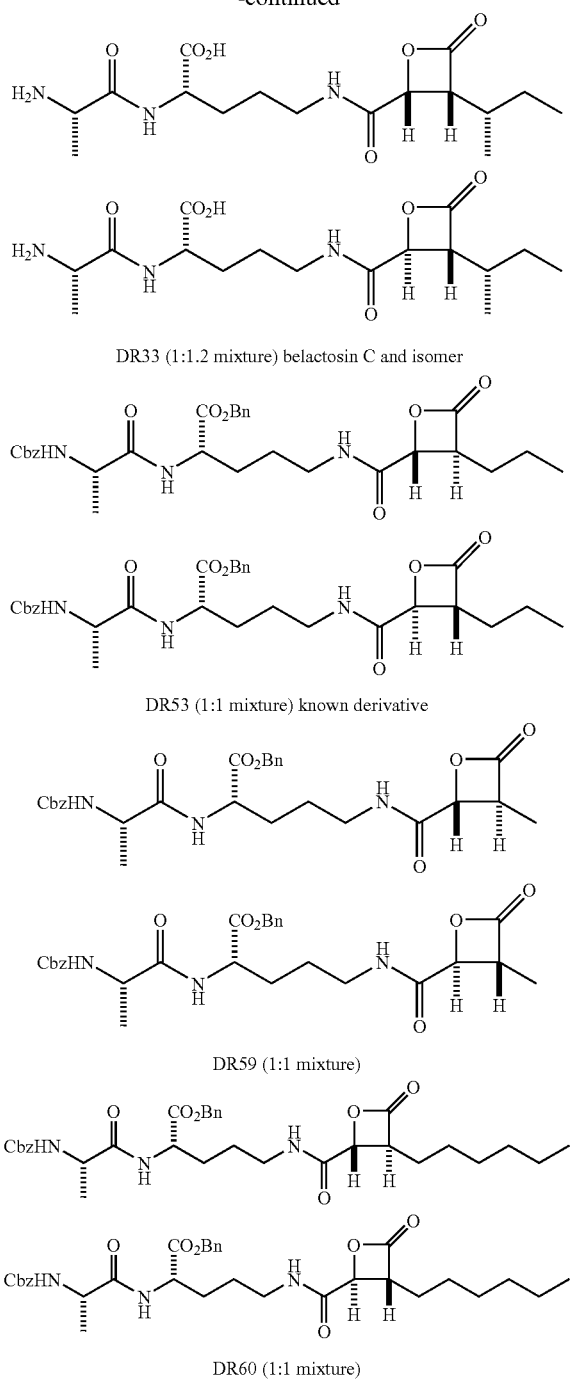

DR33 (1:1.2 mixture) belactosin C and isomer

DR53 (1:1 mixture) known derivative

DR59 (1:1 mixture)

DR60 (1:1 mixture)

Example 14

Inhibition of Fatty Acid Synthase Thioesterase Domain

Known and novel belactosin derivatives inhibit the turnover of a fluorogenic substrate by fatty acid synthase thioesterase. The thioesterase (230 nM) was incubated with a range of test compound concentrations (100 μM to 0.16 μM) and 120 μM 4-MU-heptanoate substrate, approximately 3.5× $K_m$. Fluorescence measurements were taken every five minutes at $^{350}/_{450}$ nm. Results shown are the calculated IC$_{50}$ value and corresponding 95% confidence intervals from a dose-response curve fit of the data in triplicate. See Example 13 for compounds tested.

TABLE 1

Inhibition of the Fatty Acid Synthase Thioesterase Domain

| Designation | FAS TE $IC_{50}$ (µM) | 95% CI (µM) |
|---|---|---|
| DR32 | 0.17 | 0.13 to 0.21 |
| DR33 | 26.55 | 20.48 to 34.42 |
| DR53 | 3.98 | 3.35 to 4.61 |
| DR59 | 2.86 | 1.11 to 4.60 |
| DR60 | 0.16 | 0.13 to 0.19 |

All of the compositions and/or methods disclosed and claimed in this specification can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Provisional Application entitled, "Cyclic-fused beta-Lactones and Their Synthesis," by Daniel Romo, Huda Henry-Riyad, Gil Ma, Changsuk Lee, Henry Nguyen, Seongho Oh and Vikram C. Purohit, filed Jul. 9, 2007.
PCT International Pub. No. WO 04/007506
PCT International Pub. No. WO 00/043000
U.S. Pat. No. 7,223,745
Adams et al., Cancer Res. 59:2615-22, 1999.
Adams et al., Invest. New Drugs 18:109-21, 2000.
Adams et al., Curr. Opin. Chem. Biol. 4:493-500, 2002a.
Adams et al., Trends Mol. Med. 8:S49-54, 2002b.
Akaishi et al., Brain Res., 722:139-144, 1996.
Alo et al., Cancer, 77:474, 1996.
Arionov and De Meijere, Org. Lett., 6:2153, 2004.
Armstrong and Scutt, Chem. Commun., 7(5):510-511, 2004.
Asai et al., Biochem. Pharm. 67:227-34, 2004.
Asai et al., J. Antibiot., 53:81-83, 2000.
Bodansky, "Peptide Chemistry," $2^{nd}$ ed., Springer-Verlag, New York, 1993.
Bundgaard, H., Design of Prodrugs, pp. 7-9, 21-24, Elsevier, Amsterdam 1985.
Bundgaard, Drugs of the Future, 16:443-458, 1991.
Browne, FASEB J., 20:2027-35, 2006.
Chakravarty et al., Proc. Natl. Acad. Sci. USA, 101:15567-72, 2004.
Cresswell et al., Immunol. Rev., 172:21-28, 1999.
Cho and Romo, Org. Lett., 9:1537-1540, 2007.
FluoProbes® BioDirectory of Fluorescence.
Funabashi et al., J. Biochem., 105:751, 1989.
Ganzler et al., Hum. Pathol., 28:686, 1997.
García-Echeverría, Mini Rev. Med. Chem., 2:247-259, 2002.
García-Echeverría, Int. J. Pep. Res. Ther., 12:49-64, 2006.
Grant, In: Synthetic Peptides, Freeman & Co., New York, 1992.
Greene & Wuts, In: Protective Groups in Organic Synthesis, $3^{rd}$ ed., John Wiley & Sons, New York, N.Y., 1999.
Groll et al., Chembiochem, 6:222-256, 2005.
Groll et al., Proc. Natl. Acad. Sci. USA, 103:4576-79, 2006.
Hirano et al., Methods Enzymol. 399:227-240, 2005.
Knowles et al., J. Biol. Chem., 79:30540, 2004.
Kridel et al., Cancer, 64:2070-5, 2004.
Kuhajda et al., Proc. Natl. Acad. Sci. USA, 91:6383, 2004.
Kuhajda et al., Proc. Natl. Acad. Sci. USA, 97:3450, 2000.
Kumaraswamy et al., J. Org. Chem. 71:337-340, 2006.
Kumaraswamy and Markondaiah, Tet. Lett., 48:1707-1709, 2007.
Larionov and de Meijere, Org. Lett., 6:2153, 2004.
Maier et al., Science, 311:1258, 2006.
Mellgren, J. Biol. Chem., 272:29899-903, 1997.
Michalek et al., Nature, 363:552-554, 1993.
Mizukami et al., Chem. Abstr., 126:338840, 1997.
Molecular Probes, The Handbook—A Guide to Fluorescent Probes and Labeling Technologies, $10^{th}$ Ed., 2005.
Murray et al., Anticancer Drugs 11:407-417, 2000.
Pizer et al., Cancer Res., 56:745-51, 1996.
Pizer et al., Cancer Res., 56:1189-1193, 1996a.
Pizer et al., Cancer Res., 56:2745-2747, 1996b.
Pizer et al., Cancer Res., 58:4611-4615, 1998.
Pizer et al., Cancer Res., 60:213-218, 2000.
Pizer et al., Prostate, 47:102-110, 2001.
Prasad and Chandrakumar, Tetrahedron. Asymmetry 1:1897, 2005.
Purohit et al., J Org. Chem. 71:4549-58, 2006.
Remington's Pharmaceutical Sciences, 18th Ed. Mack Printing Company, 1990.
Rossi et al., Mol. Cancer. Res., 1:707, 2003.
Simon et al., Science, 311:1263, 2006.
Swinnen et al., Int. J. Cancer, 98:19, 2002.
Ugai et al., J. Biochem. (Tokyo), 113:754-768, 1993.

What is claimed is:
1. A compound of the following formula:

wherein W is H, alkyl, aryl or a carboxylic acid protecting group;
$R_1$ and $R_3$ are each independently selected from the group consisting of H, alkyl, aryl and an amine protecting group;
$R_5$ is H, alkyl, aryl, an amine protecting group or wherein m equals 1-5 and X is a fluorophore;

R₇ is selected from the group consisting of H, alkyl and aryl;

R₈ is alkyl

R₉ is alkyl or OR₁₀, wherein R₁₀ is alkyl; and n equals 1-7;

and diastereomers and optical isomers thereof.

2. The compound of claim 1, wherein R₁ is an amine protecting group, and diastereomers and optical isomers thereof.

3. The compound of claim 1, wherein R₅ is an amine protecting group, and diastereomers and optical isomers thereof.

4. The compound of claim 1, wherein R₇ is alkyl further defined as —CH₃, and diastereomers and optical isomers thereof.

5. The compound of claim 1, wherein R₅ is

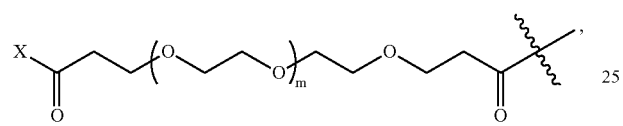

and diastereomers and optical isomers thereof.

6. The compound of claim 5, wherein m is 1, and diastereomers and optical isomers thereof.

7. The compound of claim 5, wherein X is selected from the group consisting of:

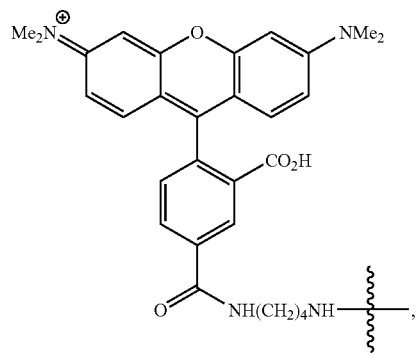

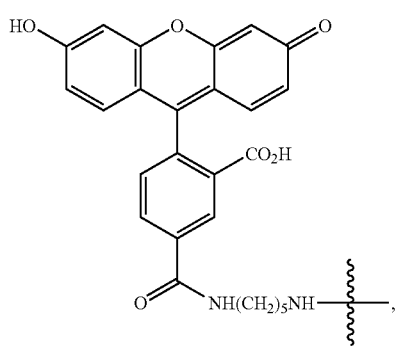

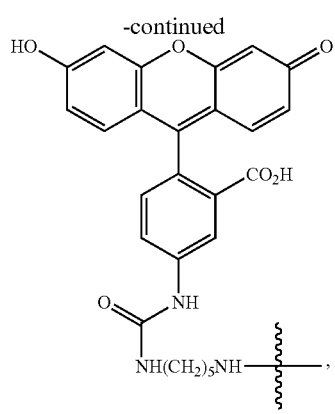

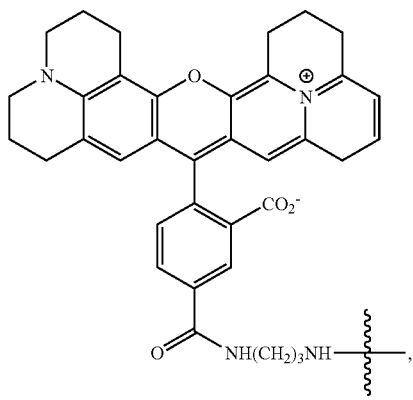

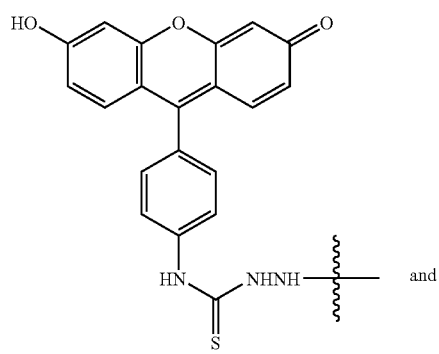

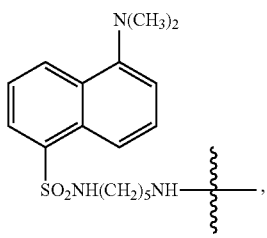

and diastereomers and optical isomers thereof.

8. The compound of claim 1, wherein R₁ is H, and diastereomers and optical isomers thereof.

9. The compound of claim 1, wherein R₃ of the compound is H, and diastereomers and optical isomers thereof.

10. The compound of claim 1, wherein n equals 1-5, and diastereomers and optical isomers thereof.

11. A compound having the formula:

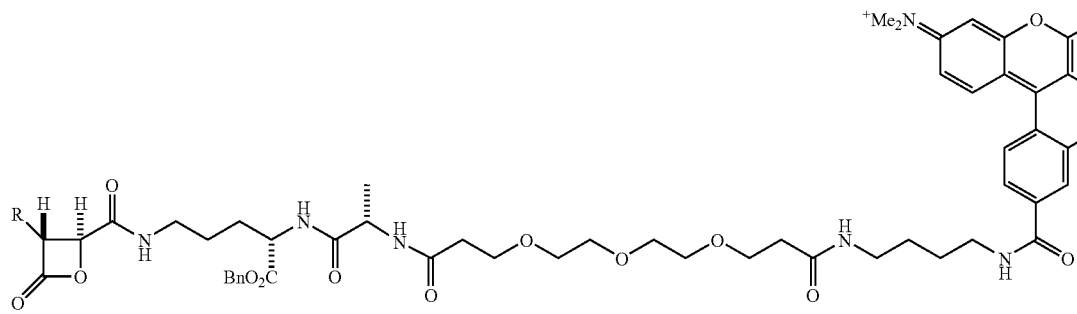

wherein R is alkyl or aryl, and diastereomers and optical isomers thereof.

12. A compound having the formula:

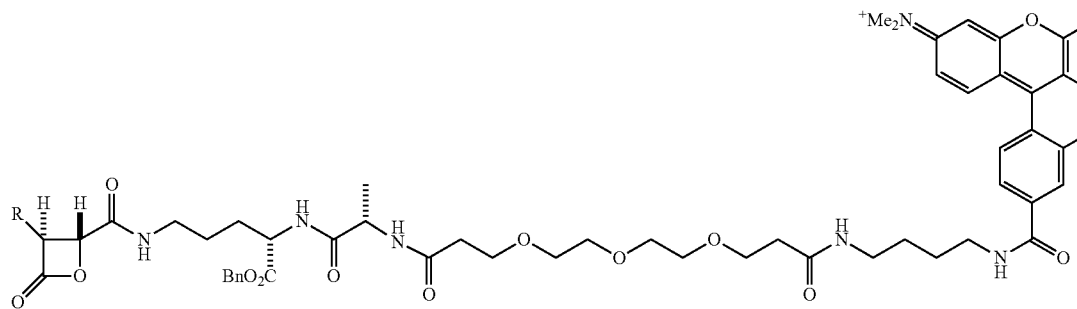

wherein R is alkyl or aryl, and diastereomers and optical isomers thereof.

13. The compound of claim 1, wherein the compound is comprised in a composition, wherein the composition comprises a pharmaceutically acceptable excipient or diluent.

14. A method of synthesizing a compound of the following formula:

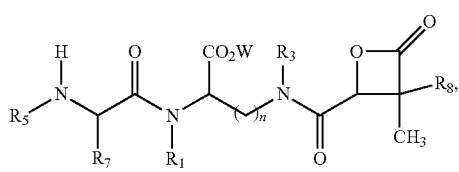

(1)

comprising:
reacting a first compound of formula (1a)

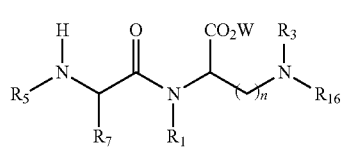

(1a)

and diastereomers and optical isomers thereof, wherein
W is H, alkyl, aryl or a carboxylic acid protecting group;
$R_1$ and $R_3$ are each independently selected from the group consisting of H, alkyl, aryl and an amine protecting group;
$R_5$ is H, alkyl, aryl, an amine protecting group or

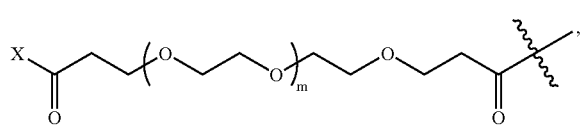

wherein m equals 1-5 and X is a fluorophore;
$R_7$ is selected from the group consisting of H, alkyl and aryl;
$R_{16}$ is selected from the group consisting of H, —C(O)C(O)H and —C(O)C(O)R$_{17}$,
wherein $R_{17}$ is selected from the group consisting of alkyl and aryl; and
n equals 1-7, and
with a second compound of formula (1b)

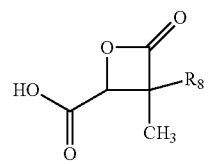

(1b)

and diastereomers and optical isomers thereof,
wherein $R_8$ is alkyl,
in the presence of a coupling agent.

15. The method of claim 14, wherein $R_5$ is an amine protecting group.

16. The method of claim 14, wherein $R_7$ is alkyl further defined as —$CH_3$.

17. The method of claim 14, wherein $R_5$ is an amine protecting group and $R_7$ is alkyl further defined as —$CH_3$.

18. The method of claim 14, wherein $R_5$ is

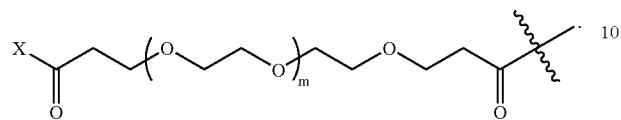

19. The method of claim 18, wherein m is 1.

20. The method of claim 18, wherein X is selected from the group consisting of:

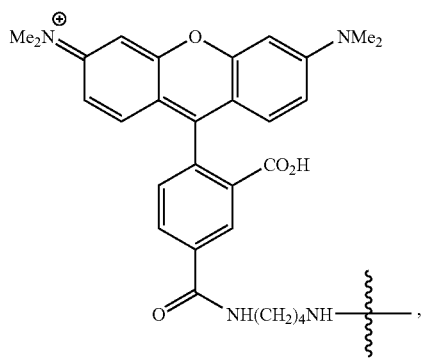

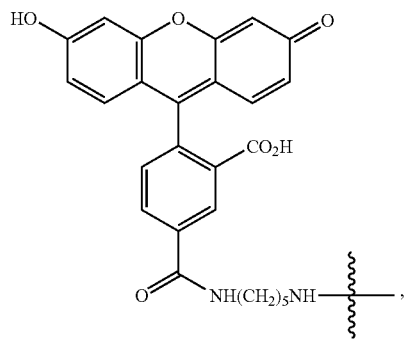

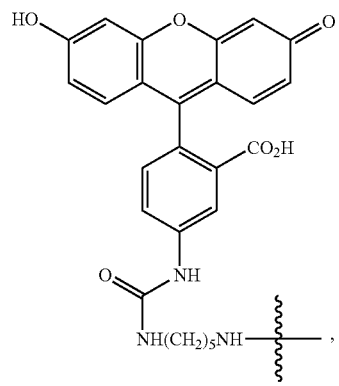

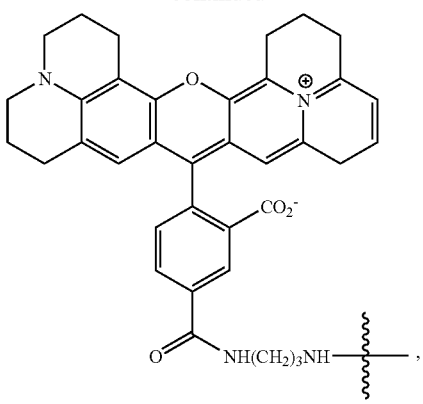

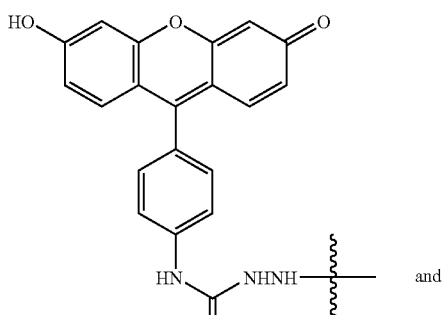

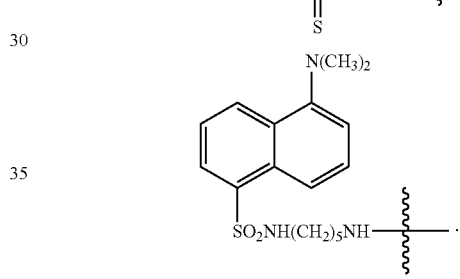

21. The method of claim 14, wherein $R_1$ is H.

22. The method of claim 14, wherein $R_3$ is H.

23. The method of claim 14, wherein $R_8$ is lower alkyl.

24. The method of claim 1, wherein n equals 1-5.

25. The compound of claim 1, further defined as:

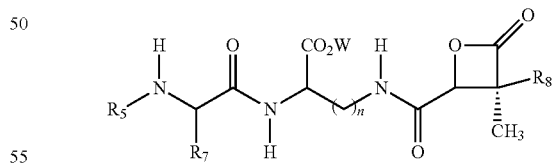

wherein:

W is benzyl, $R_5$ is an amine protecting group, $R_7$ is methyl, $R_8$ is lower alkyl, n is 1-7, and diastereomers and optical isomers thereof.

26. The compound of claim 25, further defined as:

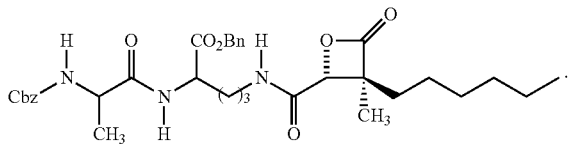

27. The compound of claim 1, wherein $R_9$ is alkyl.

28. The compound of claim 27, wherein $R_9$ is methyl.

29. The compound of claim 27, wherein alkyl is further defined as heteroatom-substituted alkyl.

30. The compound of claim 28, wherein heteroatom-substituted alkyl is further defined as —$CH_2F$, —$CHF_2$, —$CF_3$, —$CH_2SMe$, or —$CH_2OMe$.

31. The compound of claim 1, wherein $R_9$ is $OR_{10}$.

32. The compound of claim 31, wherein $R_9$ is —$OCH_3$.

* * * * *